United States Patent
Kiser et al.

(10) Patent No.: US 10,413,311 B2
(45) Date of Patent: *Sep. 17, 2019

(54) DIAPHRAGM ENTRY FOR POSTERIOR SURGICAL ACCESS

(71) Applicant: AtriCure, Inc., Mason, OH (US)

(72) Inventors: Andrew C. Kiser, Carthage, NC (US); James G. Whayne, Cary, NC (US); Sidney D. Fleischman, Durham, NC (US); Earl W. Rogers, Rougemont, NC (US)

(73) Assignee: AtriCure, Inc., Mason, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/424,449

(22) Filed: Feb. 3, 2017

(65) Prior Publication Data
US 2017/0360463 A1    Dec. 21, 2017

Related U.S. Application Data

(63) Continuation of application No. 11/408,315, filed on Apr. 21, 2006, now Pat. No. 9,561,044.
(Continued)

(51) Int. Cl.
*A61B 17/00* (2006.01)
*A61B 17/29* (2006.01)
(Continued)

(52) U.S. Cl.
CPC .......... *A61B 17/29* (2013.01); *A61B 17/3421* (2013.01); *A61B 17/3468* (2013.01); *A61M 29/02* (2013.01); *A61B 1/04* (2013.01); *A61B 17/068* (2013.01); *A61B 18/14* (2013.01); *A61B 90/37* (2016.02); *A61B 2017/00243* (2013.01); *A61B 2017/00278* (2013.01); *A61B 2017/0237* (2013.01); *A61B 2017/291* (2013.01); *A61B 2017/2906* (2013.01); *A61B 2017/2927* (2013.01); *A61B 2017/308* (2013.01); *A61B 2017/320044* (2013.01);
(Continued)

(58) Field of Classification Search
CPC .............. A61F 17/3421; A61F 17/3423; A61F 2017/3419; A61F 2017/3425; A61F 2017/0237; A61F 2017/3484; A61F 2017/3486; A61F 2017/3488; A61F 2017/000243; A61F 1/3132
See application file for complete search history.

(56) References Cited

U.S. PATENT DOCUMENTS 4,040,413 A    8/1977    Ohshiro
4,550,715 A    11/1985    Santangelo et al.
(Continued)

FOREIGN PATENT DOCUMENTS

DE    2531801    1/1976
EP    1440705    7/2004
(Continued)

OTHER PUBLICATIONS

Cragg, et al., "Endovascular diathermic vessel occlusion," *Radiology*, 144:303-308, 1982.
(Continued)

*Primary Examiner* — Diane D Yabut
(74) *Attorney, Agent, or Firm* — Levine Bagade Han LLP

(57) ABSTRACT

Methods and devices described herein facilitate diaphragm entry for posterior access of body organs.

20 Claims, 28 Drawing Sheets

Related U.S. Application Data

(60) Provisional application No. 60/726,342, filed on Oct. 12, 2005.

(51) Int. Cl.

| | | |
|---|---|---|
| *A61B 17/34* | (2006.01) | |
| *A61M 29/02* | (2006.01) | |
| *A61B 1/04* | (2006.01) | |
| *A61B 17/068* | (2006.01) | |
| *A61B 18/14* | (2006.01) | |
| *A61B 17/02* | (2006.01) | |
| *A61B 17/30* | (2006.01) | |
| *A61B 17/32* | (2006.01) | |
| *A61B 18/00* | (2006.01) | |
| *A61M 25/10* | (2013.01) | |
| *A61N 7/02* | (2006.01) | |
| *A61B 90/00* | (2016.01) | |

(52) U.S. Cl.
CPC ............. *A61B 2017/320048* (2013.01); *A61B 2017/3419* (2013.01); *A61B 2017/3445* (2013.01); *A61B 2017/3484* (2013.01); *A61B 2017/3486* (2013.01); *A61B 2017/3488* (2013.01); *A61B 2018/00291* (2013.01); *A61M 25/1002* (2013.01); *A61M 25/1011* (2013.01); *A61N 7/02* (2013.01)

(56) References Cited

U.S. PATENT DOCUMENTS

| | | |
|---|---|---|
| 5,025,778 A | 6/1991 | Silverstein et al. |
| 5,042,976 A | 8/1991 | Ishitsu et al. |
| 5,125,928 A | 6/1992 | Parins et al. |
| 5,235,966 A | 8/1993 | Jamner |
| 5,295,994 A | 3/1994 | Bonutti |
| 5,322,064 A | 6/1994 | Lundquist |
| 5,331,975 A | 7/1994 | Bonutti |
| 5,359,995 A | 11/1994 | Sewell, Jr. |
| 5,370,109 A | 12/1994 | Cuny |
| 5,467,763 A | 11/1995 | McMahon et al. |
| 5,558,665 A | 9/1996 | Kieturakis |
| 5,562,684 A | 10/1996 | Kammerer |
| 5,571,088 A | 11/1996 | Lennox et al. |
| 5,601,589 A | 2/1997 | Fogarty et al. |
| 5,716,329 A | 2/1998 | Dieter |
| 5,725,523 A | 3/1998 | Mueller |
| 5,749,879 A | 5/1998 | Middleman et al. |
| 5,762,629 A | 6/1998 | Kambin |
| 5,782,800 A | 7/1998 | Yoon |
| 5,783,227 A | 7/1998 | Dunham |
| 5,785,706 A | 7/1998 | Bednarek |
| 5,836,311 A | 11/1998 | Borst et al. |
| 5,865,802 A | 2/1999 | Yoon et al. |
| 5,919,188 A | 7/1999 | Shearon et al. |
| 5,971,983 A | 10/1999 | Lesh |
| 5,980,455 A | 11/1999 | Daniel et al. |
| 6,080,151 A | 6/2000 | Swartz et al. |
| 6,096,026 A | 8/2000 | Schultz |
| 6,161,543 A | 12/2000 | Cox et al. |
| 6,234,958 B1 | 5/2001 | Snoke et al. |
| 6,237,605 B1 | 5/2001 | Vaska et al. |
| 6,264,654 B1 | 7/2001 | Swartz et al. |
| 6,277,136 B1 | 8/2001 | Bonutti |
| 6,314,962 B1 | 11/2001 | Vaska et al. |
| 6,314,963 B1 | 11/2001 | Vaska et al. |
| 6,364,876 B1 | 4/2002 | Erb et al. |
| 6,463,332 B1 | 10/2002 | Aldrich |
| 6,468,205 B1 | 10/2002 | Mollenauer et al. |
| 6,478,028 B1 | 11/2002 | Paolitto et al. |
| 6,484,727 B1 | 11/2002 | Vaska et al. |
| 6,514,250 B1 | 2/2003 | Jahns et al. |
| 6,558,382 B2 | 5/2003 | Jahns et al. |
| 6,558,982 B1 | 5/2003 | Iguchi |
| 6,610,059 B1 | 8/2003 | West, Jr. |
| 6,613,038 B2 | 9/2003 | Bonutti et al. |
| 6,652,518 B2 | 11/2003 | Wellman et al. |
| 6,659,950 B2 | 12/2003 | Taheri |
| 6,663,622 B1 | 12/2003 | Foley et al. |
| 6,705,989 B2 | 3/2004 | Cuschieri et al. |
| 6,726,684 B1 | 4/2004 | Woloszko et al. |
| 6,887,249 B1 | 5/2005 | Houser et al. |
| 6,893,442 B2 | 5/2005 | Whayne |
| 6,917,834 B2 | 7/2005 | Koblish et al. |
| 7,063,698 B2 | 6/2006 | Whayne et al. |
| 7,144,363 B2 | 12/2006 | Pai et al. |
| 7,207,988 B2 | 4/2007 | Leckrone et al. |
| 7,371,233 B2 | 5/2008 | Swanson et al. |
| 7,485,092 B1 | 2/2009 | Stewart et al. |
| 7,628,797 B2 | 12/2009 | Tieu et al. |
| 7,749,157 B2 | 7/2010 | Bertolero |
| 7,815,571 B2 | 10/2010 | Deckman et al. |
| 2002/0165570 A1 | 11/2002 | Mollenauer et al. |
| 2003/0014037 A1 | 1/2003 | Thompson et al. |
| 2003/0018352 A1 | 1/2003 | Mollenauer et al. |
| 2003/0083688 A1 | 5/2003 | Simonson |
| 2004/0054363 A1 | 3/2004 | Vaska et al. |
| 2004/0153057 A1 | 8/2004 | Davison |
| 2004/0199196 A1 | 10/2004 | Ravo |
| 2004/0236363 A1 | 11/2004 | Kieturakis et al. |
| 2005/0020901 A1 | 1/2005 | Belson et al. |
| 2005/0251091 A1 | 11/2005 | Saadat et al. |
| 2005/0273133 A1 | 12/2005 | Shluzas et al. |
| 2006/0122462 A1 | 6/2006 | Roth et al. |
| 2006/0247499 A1 | 11/2006 | Butler et al. |
| 2006/0253181 A1 | 11/2006 | Schulman et al. |
| 2006/0293646 A1 | 12/2006 | Whayne et al. |
| 2007/0043351 A1 | 2/2007 | Fleischman et al. |
| 2007/0083082 A1 | 4/2007 | Kiser et al. |
| 2007/0083225 A1 | 4/2007 | Kiser et al. |
| 2007/0167960 A1 | 7/2007 | Roth et al. |
| 2007/0219567 A1 | 9/2007 | Bayer et al. |
| 2007/0249991 A1 | 10/2007 | Whayne et al. |
| 2008/0071568 A1 | 3/2008 | Oesterling et al. |
| 2008/0114288 A1 | 5/2008 | Whayne et al. |
| 2008/0114342 A1 | 5/2008 | Whayne et al. |
| 2008/0114354 A1 | 5/2008 | Whayne et al. |
| 2009/0143791 A1 | 6/2009 | Miller et al. |

FOREIGN PATENT DOCUMENTS

| | | |
|---|---|---|
| JP | 07-178108 | 7/1995 |
| JP | 08-322846 | 12/1996 |
| JP | 11-342107 | 12/1999 |
| JP | 2000-023898 | 1/2000 |
| JP | 2000-023989 | 1/2000 |
| WO | WO 1995/028985 | 11/1995 |
| WO | WO 1996/004952 | 2/1996 |
| WO | WO 1997/006732 | 2/1997 |
| WO | WO 2000/027290 | 5/2000 |
| WO | WO 2005/074787 | 8/2005 |
| WO | WO 2007/046860 | 4/2007 |
| WO | WO 2008/057117 | 5/2008 |

OTHER PUBLICATIONS

Gorisch et al., "Heat-induced contraction of blood vessels," *Lasers in Surgery and Medicine*, 2:1-13, 1982.

Nath, et el., "Cellular electrophysiologic effects of hyperthermia on isolated guinea pig papillary muscle: implications for catheter ablation," *Circulation*, 88:1826-1831, 1993.

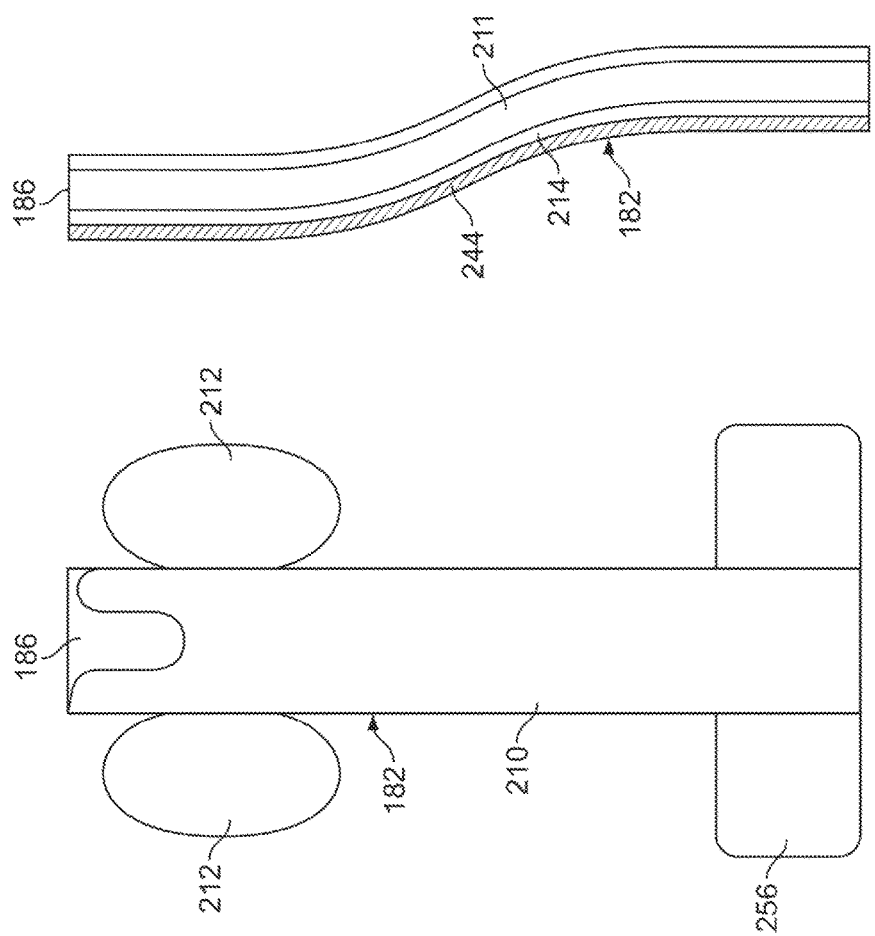

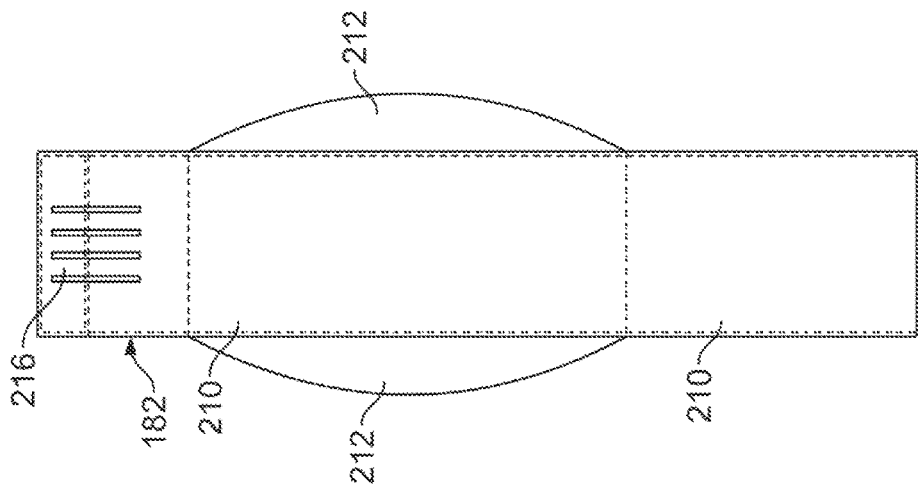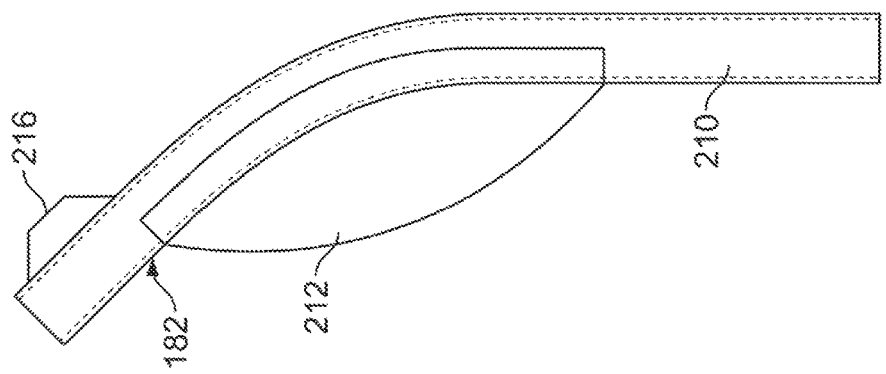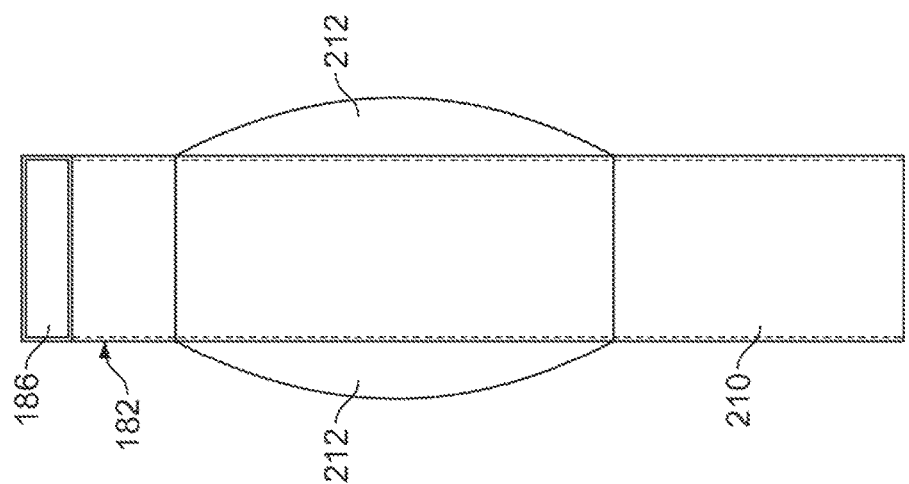

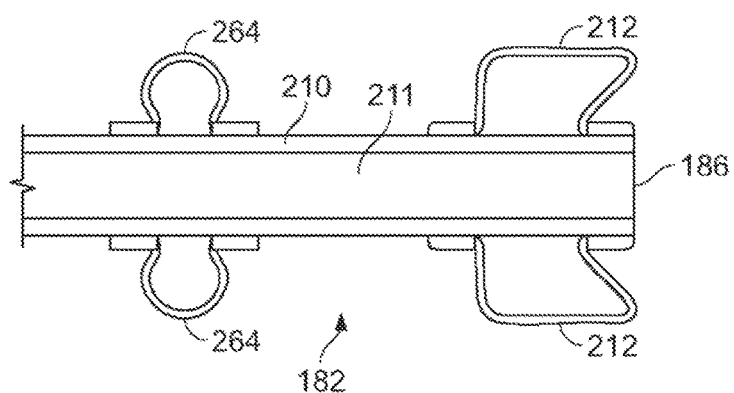
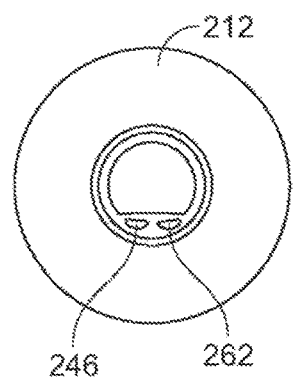
FIG. 12H  FIG. 12I
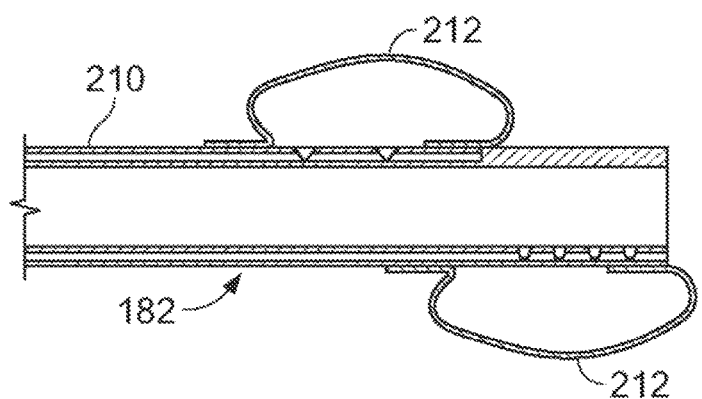
FIG. 12J

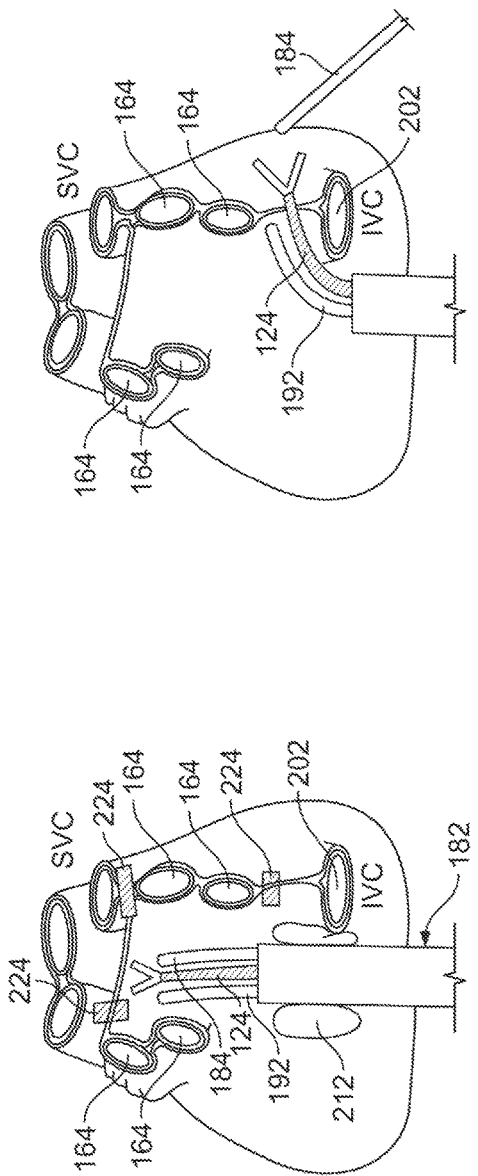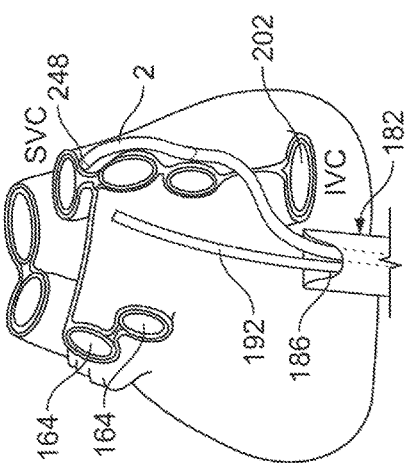

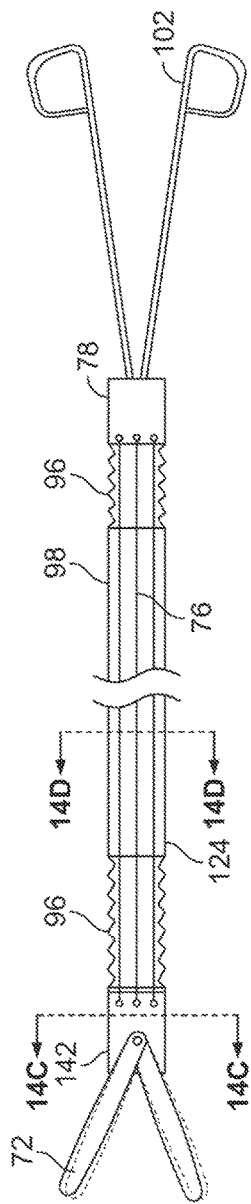
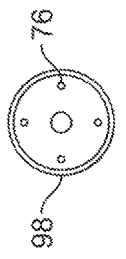
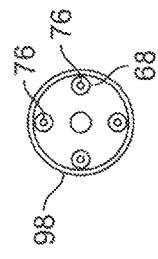
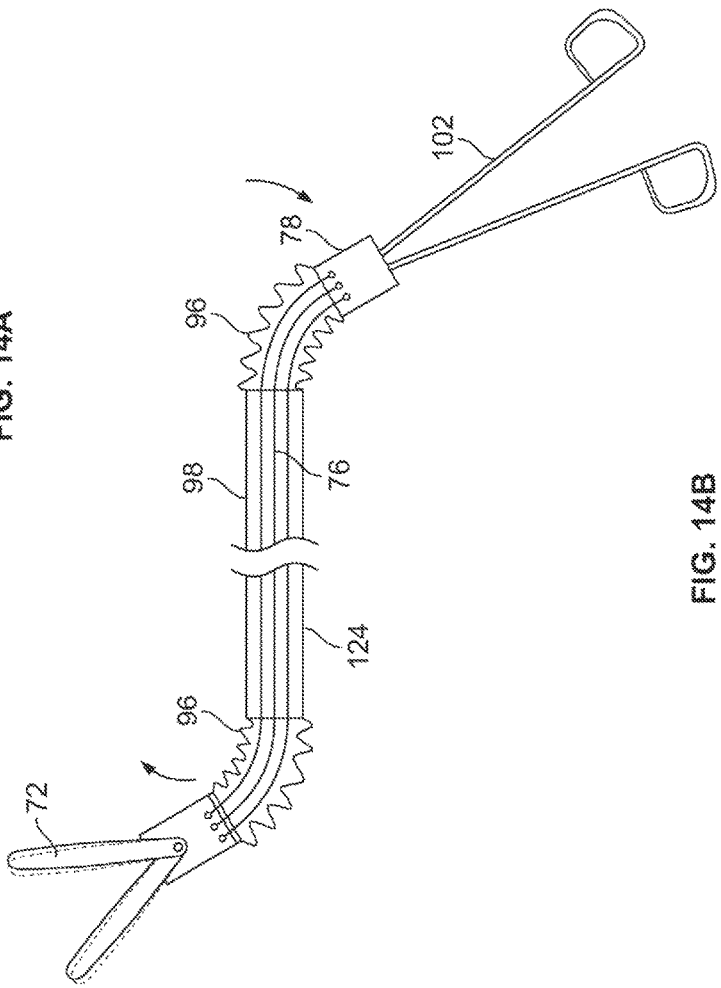

DIAPHRAGM ENTRY FOR POSTERIOR SURGICAL ACCESS

CROSS-REFERENCE TO RELATED APPLICATIONS

This application is a continuation of U.S. patent application Ser. No. 11/408,315 filed Apr. 21, 2006, now U.S. Pat. No. 9,561,044, which claims the benefit under 35 U.S.C. § 119(e) of U.S. Provisional Application No. 60/726,342 filed Oct. 12, 2005, the contents of each are incorporated herein by reference.

The subject matter of this application may be incorporated with the subject matter in the following applications: U.S. patent application Ser. No. 11/208,465 entitled "Vacuum Coagulation & Dissection Probes"; U.S. patent application Ser. No. 10/425,251 entitled "Vacuum Coagulation Probes"; U.S. Provisional application No. 60/726,342 entitled Diaphragm Entry for Posterior Access Surgical Procedures; and U.S. Pat. No. 6,893,442 the entirety of each of which is hereby incorporated by reference in their entireties.

BACKGROUND OF THE INVENTION

Field of the Inventions

Embodiments of the invention relate to methods for minimally invasive surgery and devices useful in such methods. More particularly, methods and devices described herein permit improved access within a body cavity to perform a surgical procedure, for example ablation and/or coagulation of cardiac tissue during minimally invasive surgical access to the heart. The diaphragmatic access described provides direct visualization of anatomic structures within the thoracic cavity such as the posterior left atrium, the posterior side of pulmonary veins, or any other such anatomic structure. In some variations, accessing the thoracic cavity in this manner facilitates manipulation of a coagulation probe to reliably create transmural, curvilinear lesions capable of preventing the propagation of wavelets that initiate and sustain atrial fibrillation, atrial flutter, ventricular tachycardia, or other arrhythmia substrate.

Description of the Related Art

Currently, procedures that provide access to the thoracic body cavity involve incisions through the chest wall. For example, such procedures include median sternotomy, thoracotomy, thoracostomy, or mini-sternotomy. Typically, these surgical techniques require deflation or retraction of the lungs to access the heart and/or other organs within the thoracic space.

A median sternotomy provides the most exposure for the physician. In this procedure the surgeon creates a midline incision through the sternum that cuts along the bone separating it into two sections. With a median sternotomy, although the heart can be lifted and manipulated by hand, the posterior surface of the heart or other organs is still not readily visible unless the heart is significantly rotated or lifted. However, significant rotation or lifting of the heart may cause undesirable hemodynamic issues during beating heart procedures. After the procedure, the surgeon closes the median sternotomy with large diameter metal wires. The rejoined tissue must be held stable during the healing process, similar to a bone fracture that must remain immobile during rehabilitation. Any coughing or dramatic movement is extremely painful to the patient because the chest moves. Clearly, rehabilitation after the medial sternotomy requires a significant amount of time.

Thoracotomy techniques involve creating large (or small with minithoracotomy) incisions between the ribs to gain access to the thoracic cavity. After the incision, the surgeon separates the ribs with a rib spreader to produce space for insertion of various instruments. The muscles that overlay the chest must be cut during the thoracotomy. Much of the pain during the rehabilitation process is due to the cutting of the muscles. A thoracotomy provides limited access and visualization to the heart unless endoscopes are used. Yet, even the use of endoscopes provides limited access to the posterior regions of the heart and lungs because these organs cannot be lifted or rotated easily.

Thoracostomy techniques use ports through the space created during the thoracotomy. The surgeon uses trocars (e.g. 6-10 mm) to access the thoracic cavity. Access to the anterior surface of the heart is generally sufficient with this technique. However, this technique does not provide ready access or visualization of posterior regions of the heart or other organs.

In subxyphoid techniques, the surgeon creates an incision below the xyphoid process but above the diaphragm. This technique is common for pericardiocentesis where blood is removed from the pericardial cavity during a pericardial effusion or tamponade. The diaphragm provides a barrier and hindrance to manipulating the heart or accessing the posterior heart surface during subxyphoid techniques. Accordingly, subxyphoid techniques are often limited to procedures that target the anterior or apical ventricular regions.

The conventional surgical techniques discussed do not provide the medical practitioner with sufficient visibility of anatomic structures within the thoracic cavity. For example, these procedures do not provide sufficient visibility for anatomic structures located along or adjacent to the posterior surface of the heart or lungs. In order to obtain such visibility, the patient must be placed on cardiopulmonary bypass support. Then the surgeon must create a large incision in the patient's chest through which the patient's heart and lungs can be lifted and/or rotated. Accordingly, surgical practitioners may be hesitant to treat tissues located along or adjacent to the posterior heart or lungs during less invasive procedures, given the inability to visually observe the target area. As such, minimally invasive cardiothoracic surgery has been limited to those anatomic structures located along the anterior surface of the heart.

Atrial fibrillation surgery is just one example of a surgical procedure that, while it relies on the surgical techniques discussed above, the procedure also suffers from shortcomings due to a lack of access to organs within the thoracic cavity. Atrial fibrillation surgery involving radiofrequency, DC, microwave, ultrasound, laser or other modes of thermal ablation of atrial tissue has a limitation where tissue contact throughout the length of the electrode(s) is/are not consistent. Such inconsistent electrode contact causes variability in the transmission of energy throughout the target length of ablated/coagulated tissue. This inconsistency also produces undesirable gaps of viable tissue that promote propagation of wavelets that sustain atrial fibrillation, or produce atrial flutter, atrial tachycardia, or other arrhythmia substrate. Target tissue regions that reside along the posterior surface of the heart is one factor that contributes to inconsistent electrode contact. As discussed above, conventional means of surgical access are not optimal to access the posterior surfaces.

Another factor that contributes to the inability of existing thermal ablation probes to create complete curvilinear, transmural lesions is the presence of convective cooling on the opposite surface of the atrium. This convective cooling produces a heat sink that decreases the maximum temperature at the surface thereby preventing the lesions from consistently extending transmural through the entire wall of the atrium. This phenomenon is especially significant during beating-heart therapies where the surgeon places the coagulation/ablation probe against the epicardial surface. However, because blood is still flowing along the endocardium, the blood removes heat. Heat convection produces a larger temperature gradient between tissue immediately under the probe electrodes along the epicardium and tissue at the endocardium. Increased tissue contact is capable of reversing this effect through compression of the tissue. This reduces the effective the wall thickness of the atria, ensuring consistent contact throughout the length of the electrode(s), and increasing the efficiency of thermal conduction from the epicardium to the endocardium creating a more consistent and reliable lesion.

Another deficiency of current approaches is the inability to direct the coagulation to precise regions of soft tissue while avoiding underlying or nearby tissue structures. For example, atrial fibrillation ablation may involve extending a lesion to the annulus near where the circumflex, right coronary artery and coronary sinus reside. In another example, atrial fibrillation involves ablating ventricular tachycardia substrates residing near the coronary arteries or coronary veins. In a third example, the esophagus resides along the posterior left atrium between the left and right pulmonary veins; unanticipated heating of the esophagus during atrial fibrillation treatment can produce esophageal fistulas which can be associated with high morbidity and mortality rates. Conventional approaches cannot selectively ablate the desired soft tissue structures while isolating other tissue structures that are intended to be preserved from targeted regions.

The improved methods and devices described herein offer improved access to tissue regions within the body, especially those organs in the thoracic cavity. Variations of these methods and devices address the above described deficiencies for atrial fibrillation and ventricular tachycardia ablation. In addition, the embodiments or variations of the embodiments may address similar deficiencies, which are apparent during other applications involving coagulation of a selected tissue region in a precise manner.

SUMMARY OF THE INVENTION

The devices described herein allow for creating a temporary cavity between organs in a body. Generally, the devices include an elongate member having at least one working channel extending therethrough, the elongate member having a distal portion adapted for insertion into the body and a proximal portion, the elongate member having sufficient column strength to allow insertion of the distal portion between organs, at least one opening at a distal end of the elongate member, where the working channel(s) exits the elongate member at the opening(s), and a first expandable member adjacent to the distal portion adapted to expand about the elongate member, where upon expansion between organs the first expandable member separates the organs to form the temporary cavity around the opening(s). In variations of the invention, an access device may have an additional working channel (referred to as a working lumen) that is intended to allow insertion and removal of various devices in the main working channel without disturbing a device (e.g., a scope) that is left at the surgical site in the working lumen.

Variations of the access device include expandable members that are configured to expand non-uniformly about the elongate member. As discussed below, this configuration may permit improved formation of a temporary cavity.

In another variation, the elongate body may be tapered increasingly from a distal portion to the proximal portion. This tapering provides several advantages such as: causing natural separation of organs as the elongate member is further advanced between organs, facilitating easier manipulation of multiple instruments through the elongate member (given the larger size of the proximal working channel), and increases the maneuverability of instruments within the elongate member.

The devices may also include a proximal portion of the elongate member that allows manipulation of the access device outside of the body. For example, the proximal portion may have one or more handles or grips that are commonly known and used in medical devices.

The access devices described herein may be constructed to have lengths that are slightly greater than the lengths of standard scopes. In this manner, a scope advanced through the device will be placed at the temporary cavity, reducing the risk that the scope may be advanced through the temporary cavity and cause unintended damage.

Variations of the device further include one or more shapeable support members coupled to the elongate member, where the shapeable support member causes the elongated member to retain a shape of the shapeable support member. The shapeable support member may be placed in a support lumen. In one example, a shapeable support may be formed or shaped outside of the device by the medical practitioner. Upon achieving the desired shape, the support member is advanced within the support lumen causing the device to conform to the desired shape.

The expandable members described herein include balloons, or strand-like support members. Any number of expandable members may be used on a device. In some variations, the expandable support member (or a portion thereof) extends beyond the distal end of the elongate member. This feature permits clearance between the end of the device and body tissue or fluids.

The balloons or support members described herein may be of any shape as described below. In addition, the expandable members may include features (e.g., grooves, coatings, etc.) that assist in separating, elevating and/or stabilizing tissue or organs. The expandable members may be expanded independently of each other or may be constructed to expand together.

The devices described herein may include any number of suction ports at the end or within the working channel of a device. Furthermore, the device may include visualization elements to aid in observing the surgical platform in the temporary cavity.

The devices described herein may also include locking features that assist in securing the device within the body. For example, the device may include a set of locking balloons located proximally on the elongate member where the balloons secure the device within the body or to an outside surface of the body just adjacent to the incision.

Variations of access devices also include expandable members that are slidable into and out of the elongate member. These expandable members may have any number of sets of arms that separate and elevate organs to create the temporary cavity.

Methods are also described herein, where the methods allow for accessing posterior surfaces of a body organ in a patient via a minimally invasive procedure by accessing a diaphragm through a first incision in an abdomen of the patient, creating an opening in the diaphragm, advancing an access device through the diaphragm into the thoracic cavity, where the access device comprises at least at least one working channel and an expandable member on an exterior of the device, and forming a temporary cavity by actuating the expandable member to separate adjacent tissue structures in the thoracic cavity.

The methods include use of a visualization system coupled to the working channel or inserting a scope-type device into the working channel to provide visual access to the posterior surface of the organ.

The methods described herein include creating a temporary cavity on surfaces of the heart where the access device is placed in the thoracic cavity between the heart and spine. The temporary cavity may be formed on other organs such as an esophagus, and actuating the expandable member to separate the esophagus from esophageal vessels.

Methods are also described to treat a body organ in a thoracic cavity of a patient via a minimally invasive procedure by accessing a diaphragm through a first incision in an abdomen of the patient, placing a device having at least one ultrasound transducer coupled thereto against a surface of the diaphragm, and applying ultrasound energy through the diaphragm to tissue within the thoracic cavity.

Variations of the access device and procedures described above include combinations of features of the various embodiments or combination of the embodiments themselves wherever possible.

BRIEF DESCRIPTION OF DRAWINGS

FIGS. 7A to 7C show a top view, a side-sectional view, and a cross-sectional view of an variation of an access device for use as described herein;

FIGS. 8A to 8C show a top view, a side view, and a bottom view of another variation of an access device;

FIGS. 12D to 12J show additional variations of access devices;

FIGS. 13A to 13C show perspective views of a dissecting instrument embodiment manipulated during the Diaphragm Entry for Posterior Access process of the invention to further define a cavity into which instruments may be manipulated;

FIG. 14A shows a side view of a dissecting instrument embodiment in a non-actuated configuration;

FIG. 14B shows a side view of the dissecting instrument in FIG. 14A in an actuated configuration;

FIGS. 14C and 14D show cross-sectional views taken along section A-A and B-B through the dissecting instrument in FIG. 14A;

DETAILED DESCRIPTION

Methods and devices described herein provide for improved manipulation of organs and/or instruments in the thoracic cavity. The methods and devices may allow for direct visualization along the posterior region of the heart and other anatomic structures not attainable with conventional thoracic approaches. Furthermore, the methods and devices described herein may be used in conjunction with, or as an alternative to the conventional approaches described herein. In general, the surgical approaches and procedures described herein rely on entry through the diaphragm of a patient to access a posterior region of that patient (the procedure hereafter referred to as "Diaphragm Entry for Posterior Access" or simply "DEPA"). The DEPA procedure may also be referred as VAPS (Video-Assisted Pericardiac Surgery) or TAPS (Trans-Abdominal Pericardiac Surgery).

Figure 1B:
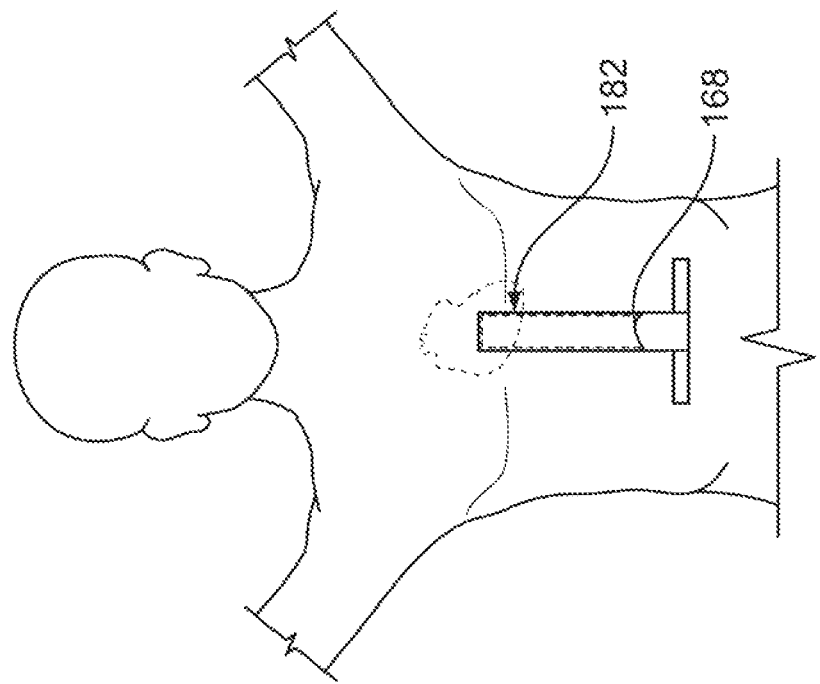
FIGS. 1A and 1B show top views of patients with two Diaphragm Access process embodiments of accessing the thoracic cavity to manipulate coagulation, dissection, and visualization devices.
Figure 1A:
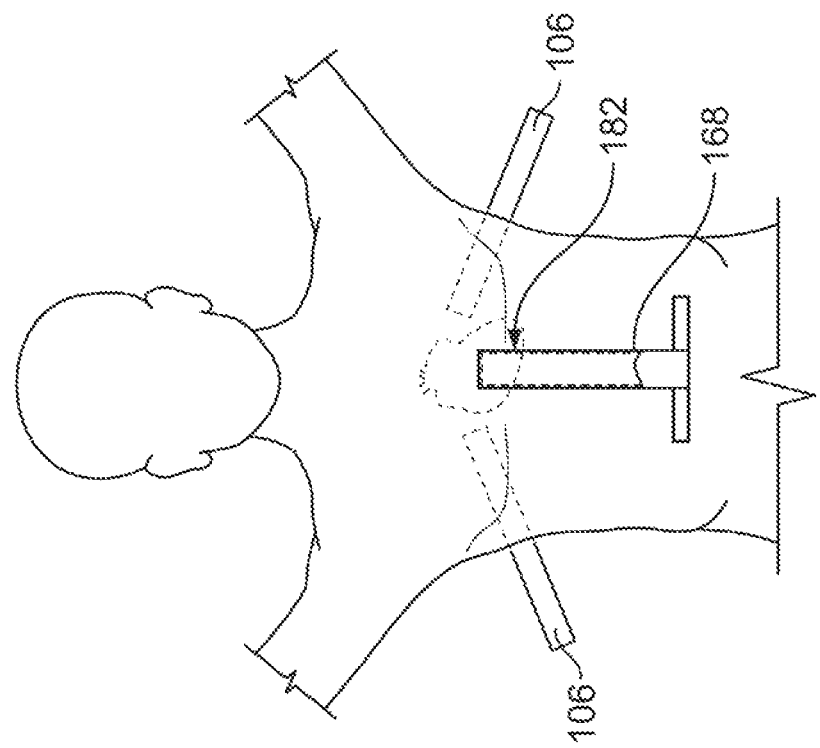

FIGS. 1A to 1B show examples of placement of access devices 182 (also referred to as a separator or an elevator herein) under the methods for posterior access. Once a patient is prepared, as discussed in the examples below, an access device 182 is inserted through, at least a first, an abdominal, incision 168. The device is then advanced through the diaphragm (not shown) and placed adjacent or between organs for creation of a temporary cavity. FIG. 1A illustrates one example, in this variation, the surgeon places the access 182 between heart and the spine such that the esophagus can be separated from the posterior surface of the heart.

As shown in FIG. 1A, the method may be augmented with one or two additional thoracostomy incisions allowing for placement of trocars 106 into the thoracic cavity. The trocars 106 permit insertion of surgical tools or visualization devices. Accordingly, the access device 168 allows for direct visualization of the posterior surface of the organs during manipulation of the instruments inserted through the right and/or left thoracostomy access ports 106. Moreover, use of the additional thoracostomy access sites with the access device 168 may permit the surgeon to visualize the anterior surfaces of anatomic structures, during the procedure. Once tissue obscures the surgical site from the surgeon's view via the thoracostomy access ports 106, the access device 168 allows the surgeon to have a posterior view of the surgical site. As shown in FIG. 1B, variations of the methods described herein include posterior access techniques using an access device 168 without additional thoracostomy access ports.

Figure 1C:
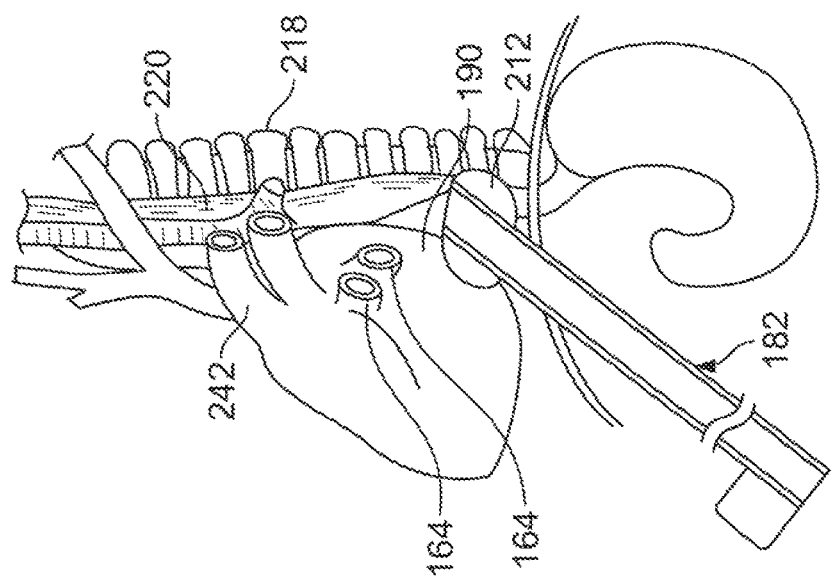
FIGS. 1C and 1D show a partial side view of the thoracic cavity and demonstrates an example of insertion of an access device into the abdominal space and ultimately into the thoracic cavity.
Figure 1D:
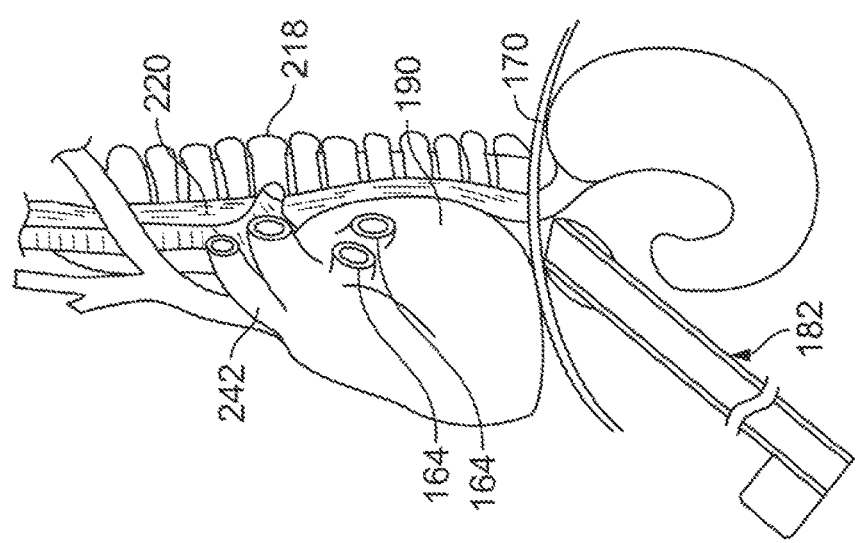

FIGS. 1C to 1D illustrate partial cross sectional views of a patient's thoracic cavity and abdomen to demonstrate a general principle of the DEPA procedure. For the sake of clarity, certain organs are not shown in the figures. FIG. 1C illustrates the DEPA procedure after the patient is prepared (as discussed herein) and after the DEPA incision is made within the abdomen. As shown, the DEPA incision allows entry of an access device 182 within the abdominal space and adjacent to a diaphragm 170. An incision in the diaphragm may be made using cutting features incorporated in the access device 182, a tool advanced through the access device 182, or via another tool advanced through another abdominal port or a thoracostomy port.

FIG. 1D shows an example of an access device 182 as it creates a temporary space within the thoracic cavity by separating the posterior ventricular surface 190 of the heart from the spine 218 and esophagus 220. As discussed below, the methods described herein contemplate creation of a temporary cavity about any organ such that the access device separates one or more additional organs from the desired surgical space. FIG. 1D shows the expansion of expandable members 212 (e.g., as discussed below: inflatable bladders, expandable strands, etc.) to separate adjacent tissues and form a temporary cavity. In the variation shown, the access device 182 creates the temporary cavity at a posterior surface of the heart. As described below, the temporary cavity may be formed where needed including the various other organs and/or tissue surfaces within the body. This temporary cavity permits improved surgical and visual access to various tissue surfaces without the use of complex equipment. In general, the improved access provides the surgeon the ability to perform additional procedures that would otherwise be difficult or impossible.

Figure 2B:
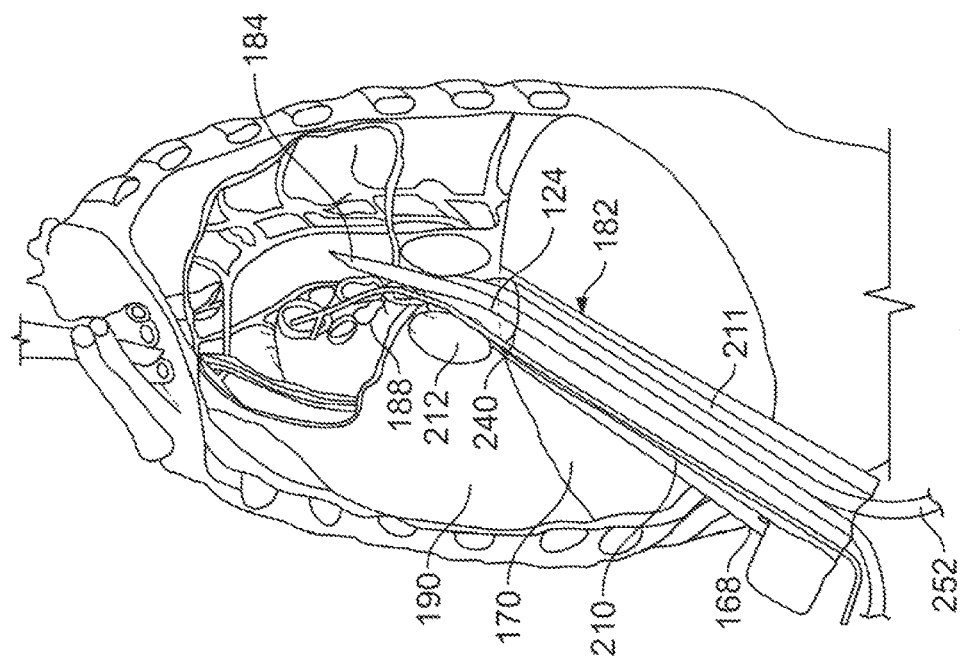
FIGS. 2A to 2C show side sectional views of a thoracic cavity with a variation of an access device used to separate the heart from posterior anatomy.
Figure 2A:
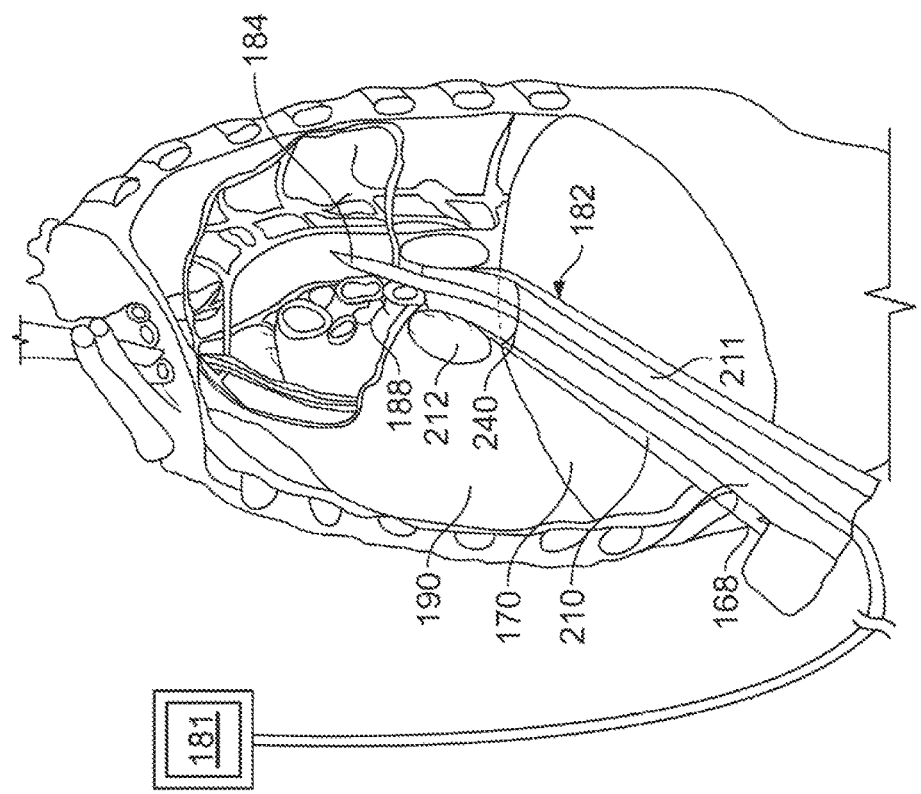
Figure 2C:
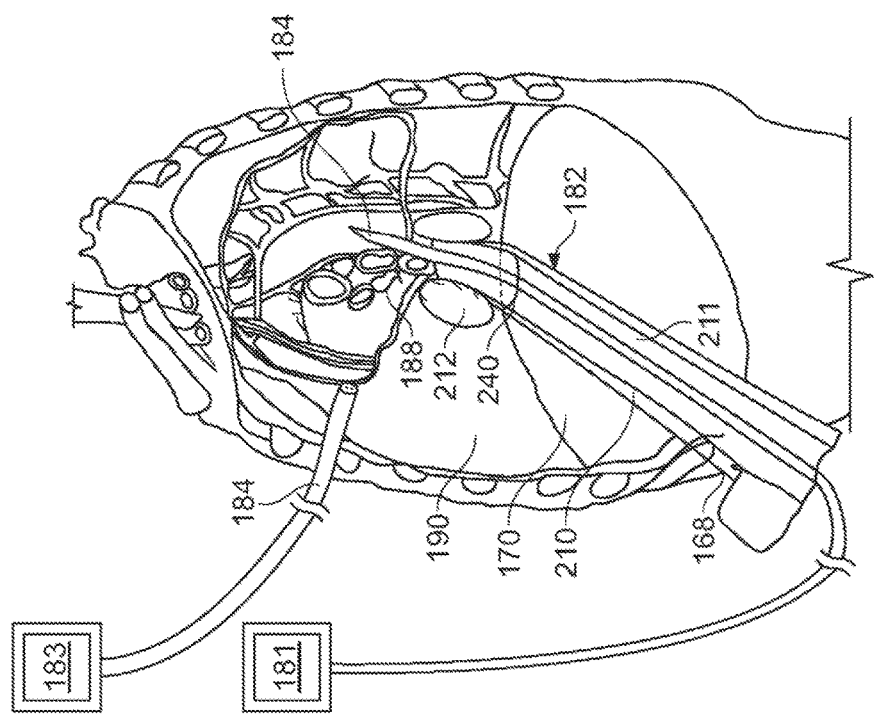

FIGS. 2A to 2C illustrate side-sectional side views of the access device 182 when inserted through an opening in the diaphragm 240. As shown, the access device 182 enters the patient through an abdominal incision 168 below the diaphragm 170. The device 182 then advances through diaphragm (e.g., via an incision 240) to access the posterior organ surfaces. As noted below, the access device 182 defines a tube 210 having at least one working channel 211 through which the instruments can be inserted and manipulated. A scope 184 (hereafter a "DEPA scope") can be used to visualize a substantial portion of the posterior heart (posterior atrium 188 and posterior ventricle 190) and/or other organs/tissue. Typically, the scope 184 transmits an image to an external monitor 181. Once the surgeon positions the device 182, expandable members 212 on the device may be actuated to create a temporary cavity within the body. In this variation, the expandable members 212 comprise inflatable bladders or balloons that expose a posterior atrial surface 188 and a posterior ventricular surface 190 of the heart.

As shown in FIG. 2A, entry into the thoracic cavity via the diaphragm allows the access device 182 to form a smooth transition/angle from the access site into the patient to the posterior surface of the organs in the thoracic cavity (e.g., heart, lungs, esophagus, etc.). The traditional approaches mentioned above require multiple steep angles that require excessive manipulation of devices and do not offer visualization without complex equipment. Such equipment introduces significant difficulty in manipulation and viewing perspective. The angle of entry provided by the access device 182 via the diaphragm 170 allows use of a straight scope, having a viewing angle between 0 and 60 degrees, to visualize the posterior surface of the organs. Flexible scopes may be used but are not necessary because of the smooth transition and shallow angle of insertion from the skin puncture site to the diaphragm incision adjacent the posterior heart surface.

Yet another benefit provided by the entry method of FIG. 2A is that a surgeon may manipulate instruments within the thoracic cavity in an easier and more controllable manner. For example, use of conventional techniques requires that a surgeon operate with a device having a near 90 degrees bend. Manipulation of such a device is difficult since pushing down directs the device away from tissue and the organs within the thoracic cavity interfere with the device when pulled upward. Use of relatively complex steerable equipment introduces complexity as well as reduces the surgeon's tactile feedback.

FIG. 2B illustrates the access device 182 positioned in the thoracic cavity as the surgeon manipulates a surgical tool 124 in the thoracic cavity. As shown, the DEPA scope 184 allows posterior visualization of the surgical site. In many cases it is important to keep the visual field clear from fluids. Accordingly, the access device 182 may have an aspiration tube 252 or separate aspiration lumen to draw fluids from the surgical site.

Figure 3A:
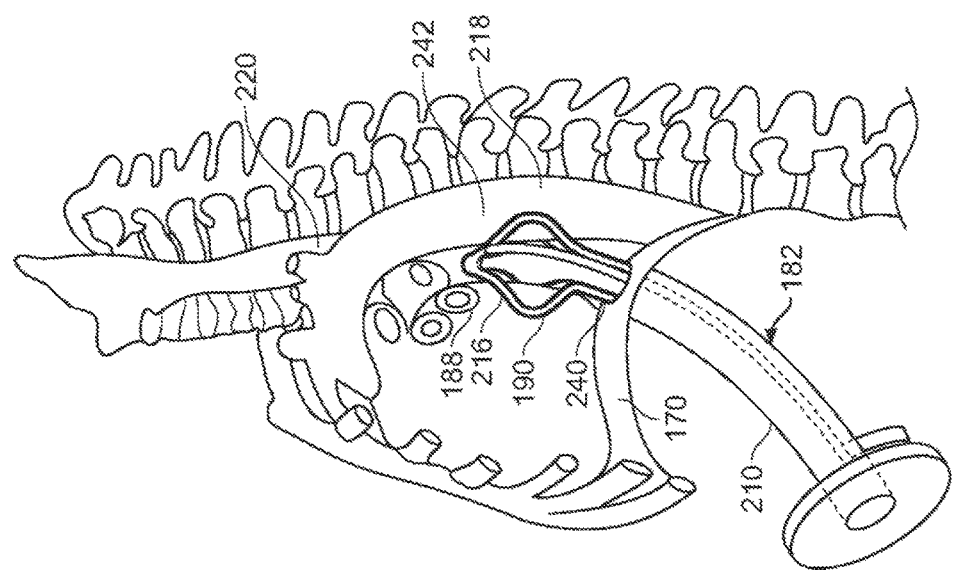
FIGS. 3A to 3C show side views of a thorax with a device as described herein defining a temporary cavity through which surgical devices may be manipulated during a surgical procedure.
Figure 3C:
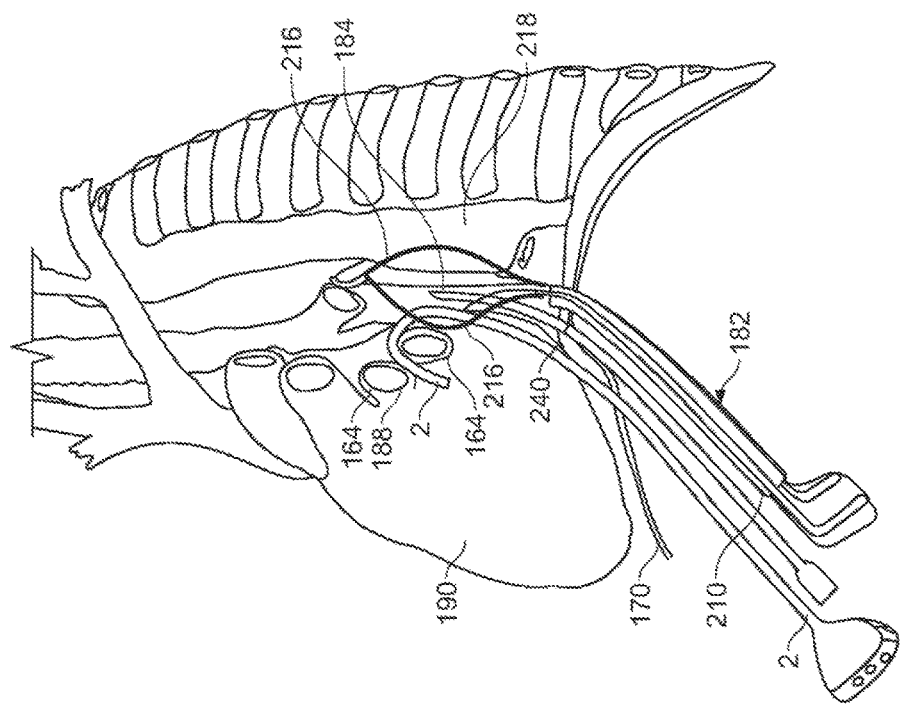
Figure 3B:
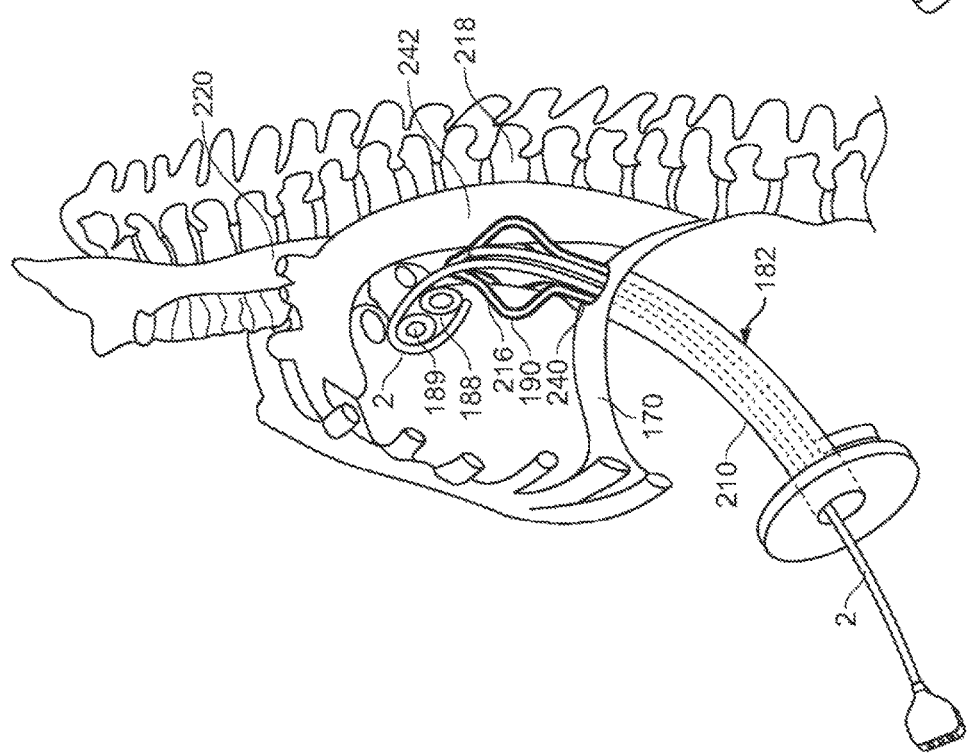

FIGS. 3A-3B, illustrate another variation of an access device 182. As shown in FIG. 3A, the device 182 includes expandable member 216 in the form of expandable stabilizer strands 216. Alternatively, as described above, the expandable member may comprise a set of balloons or bladders. FIG. 2C illustrates another variation where the surgeon positions the access device 182 in the thoracic cavity. However, in this variation, the surgeon may also use a second scope 184 advanced in a conventional manner as discussed above (e.g., through trocars 106 as shown in FIG. 1A). The purpose of the second scope 184 is to view the anterior surface of the organs. This arrangement allows visualization of the anterior and posterior surfaces of the organ. Accordingly, as a surgeon performs a procedure on an anterior or posterior surface, as the surgeon breaks through to the opposite surface (i.e., the posterior or anterior surface) use of the two scopes 182 and 184 improves visualization. In one example, the DEPA scope may be used merely for posterior visualization during a video assisted thoracostomy procedure.

FIG. 3A-3B, illustrate another variation of an access device 182. As shown in FIG. 3A, the device 182 includes expandable member 216 in the form of expandable stabilizer strands 216. Once the surgeon positions the access 182 device in place, the expandable members 216 actuate to separate the organs and define a temporary cavity. Once the surgeon completes the procedure, the expandable member 216 collapses, thereby causing closure of the temporary cavity. In this variation, the expandable members 216 separate the esophagus 220 from the descending aorta 242 while also stabilizing both organs. This action serves to protect these anatomic structures while defining the temporary cavity.

FIG. 3B illustrates placement of an ablation device 2 (e.g., as those described herein) through the working channel(s) 211 of the device 182. As shown, the temporary cavity permits visualization of a posterior surface of the organ (in this case the heart). This action allows the surgeon to ablate or treat the posterior surfaces of the heart. For example, the surgeon may treat the pulmonary veins located on the posterior surfaces on the heart without having to dissect the veins from the heart. As noted above, to keep the visual field clear from fluids, the access device 182 may have an aspiration tube or separate aspiration lumen to draw fluids from the surgical site.

Without posterior access, a surgeon would have to dissect the veins away from the heart's surface and then attempt to perform the procedure. Even in such a case, without posterior visualization, the surgeon is forced to treat portions of the veins blindly. On the other hand, a surgeon using a scope-type device (such as a DEPA scope 184 as described above), as shown in FIG. 3C, can directly visualize the posterior surfaces of the heart and veins during the treatment.

Another technique made possible through use of the access device 182 and diaphragm entry is that the surgeon can create a lesion on each side of a pulmonary vein (and in fact, an entire lesion pattern capable of treating atrial fibrillation) without having to dissect the pulmonary veins from the pulmonary artery, superior vena cava, or pericardium. The access device 182, as shown in FIG. 3B, allows the surgeon to reach the inferior surface of the pulmonary veins 189 located on the posterior atrial surface 188. Therefore, the surgeon has access along each side of the left pulmonary veins, and each side of the right pulmonary veins. Furthermore, the surgeon may apply additional lesions to the posterior surface of the heart with minimal or no dissection of the pulmonary veins.

FIG. 3C also shows another variation of the DEPA methods, where an access device 182 separates adjacent tissue to create a temporary cavity. The surgeon then may advance treatment devices 2 and visualization devices (e.g., an endoscope 184) to the temporary cavity but external to the access device 182. As shown, the treatment device 2 permits creation of a lesion on the posterior surface of the heart and on the pulmonary veins. In this variation, the access device 182 uses stabilizer strands 216, however, any variation of device may be used.

Figure 3E:
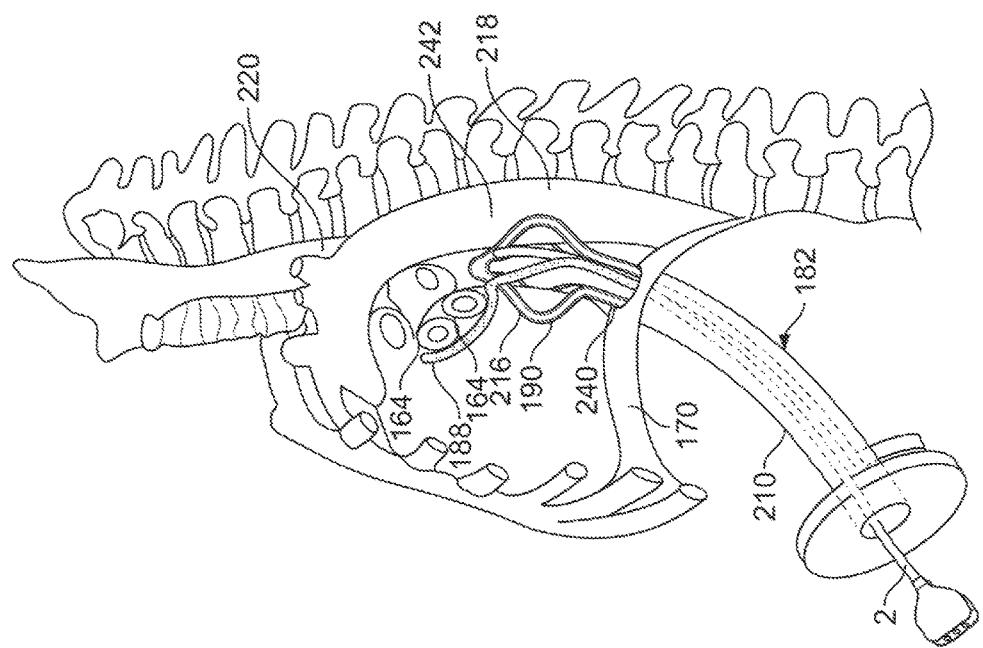
FIGS. 3D to 3F show side views of a thorax to illustrate accessing a posterior atrial surface around pulmonary veins without having to dissect tissue around the pulmonary veins.
Figure 3D:
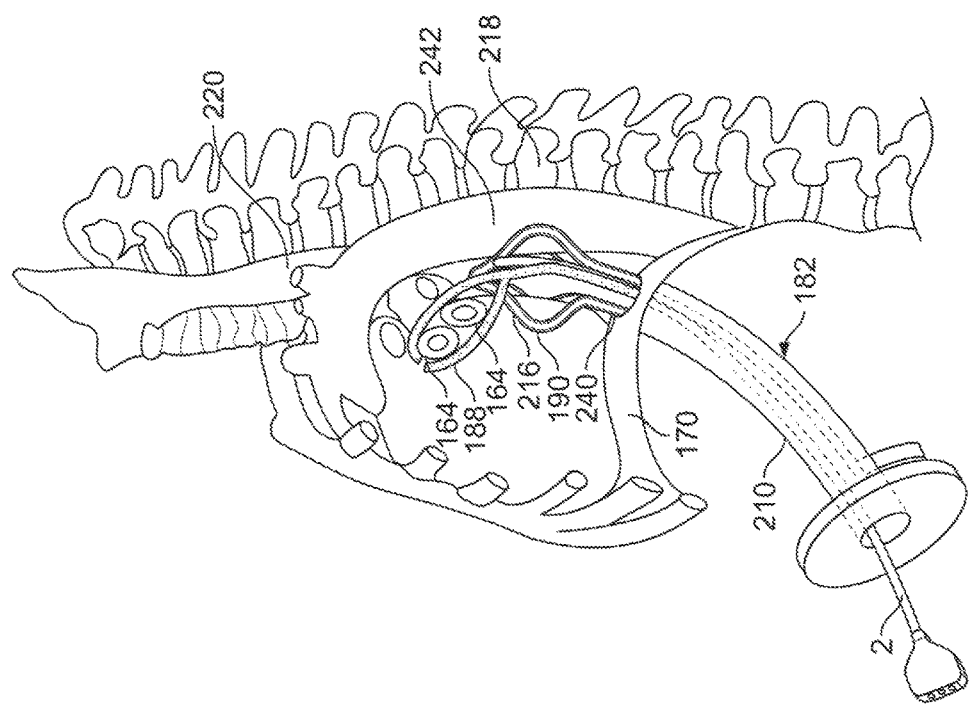
Figure 3F:
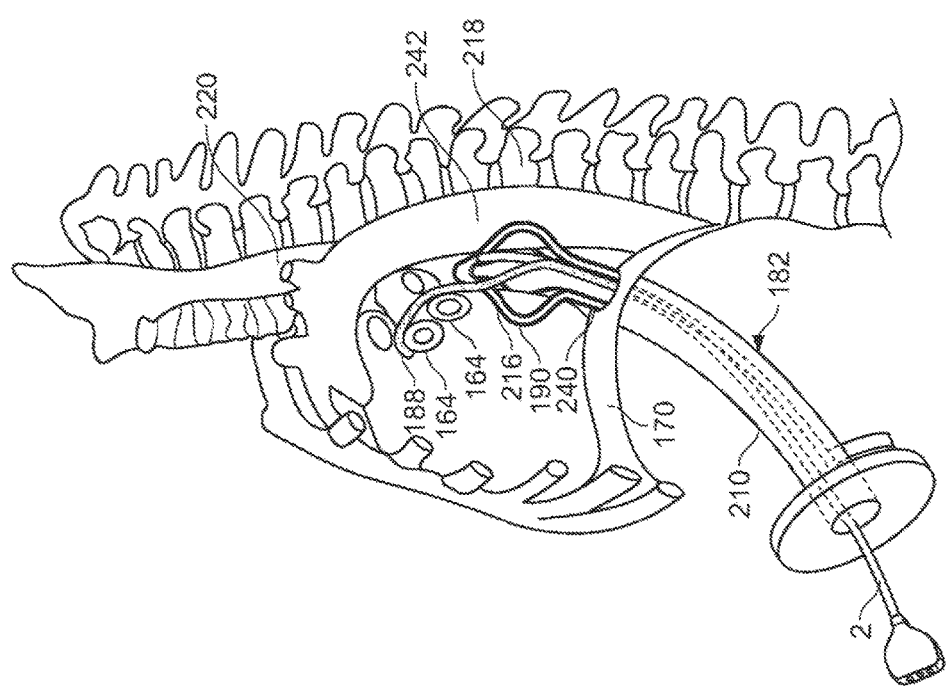

FIGS. 3D to 3F illustrate another variation of a DEPA method that is made possible because of access to the posterior region of the heart. As noted above, conventional approaches intending to apply coagulation devices to a posterior surface of the heart requires dissection of tissue to access the posterior surface. Typically, when the surgeon intends to create a coagulation line around the atrial surface adjacent to the pulmonary vein, the coagulation device is inserted around the pulmonary vein that is dissected from cardiac tissue. Because the DEPA method provides direct access to the posterior surface of the heart, the pulmonary veins and surrounding atrial surface are directly visible and accessible without dissection of tissue. As shown in FIG. 3D, a treatment device 2 can access the posterior atrial surface 188, in this case around the pulmonary veins 164, without having to dissect tissue.

FIG. 3D, illustrates a variation of a treatment device 2 that has two opposing c-type electrodes. This device allows formation of a coagulation line around the pulmonary veins. FIGS. 3E and 3F illustrate treatment devices 2 using a single c-type electrode configuration to form coagulation lines on the atrial surface 188 around each side of the pulmonary veins 164.

Figure 4B:
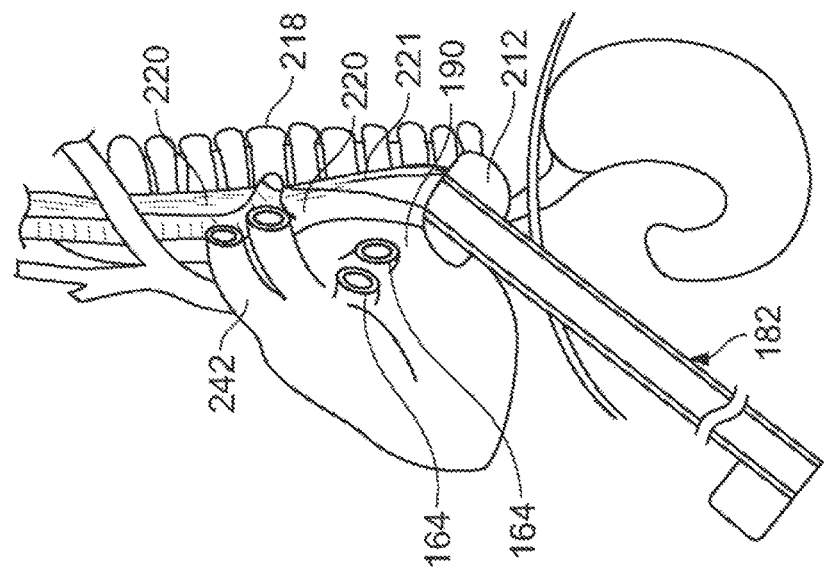
FIG. 4B shows an example of an access device separating the esophagus from associated vessels.
Figure 4A:
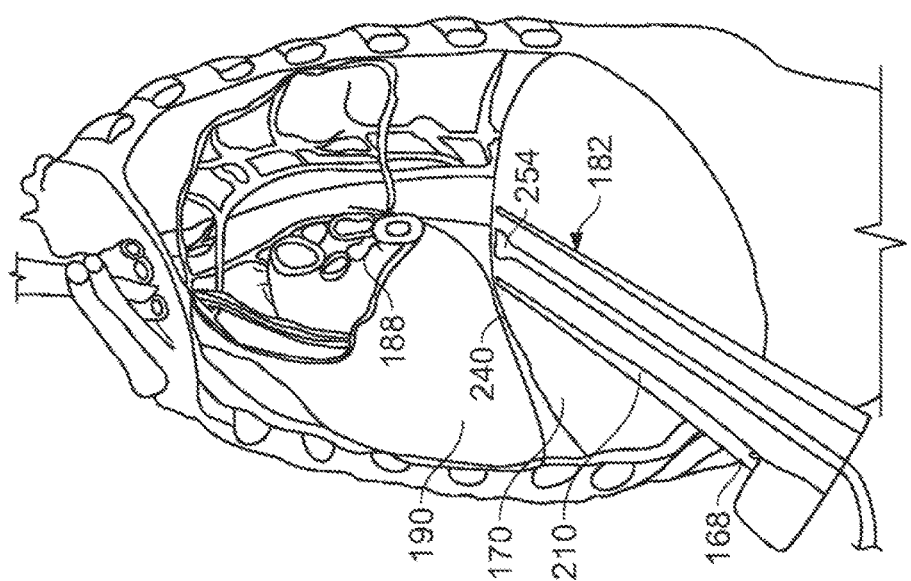
FIG. 4A shows a variation of an access device placing an ultrasound device against a diaphragm.

FIG. 4A illustrates another variation of a diaphragm-approach for treatment of tissue structures within the thoracic cavity. This approach is capable of treating thoracic tissue contacting the diaphragm without penetrating the diaphragm. The access device 182 advances to the diaphragm 240 without penetrating it. Next, the surgeon places an ultrasound-device 254 (or other ablation energy emitted by a device capable of focusing enough energy to heat tissue at distance greater than 1 inch from the device) having at least one ultrasound transducer against a surface of the diaphragm. The ultrasound device 254 focuses energy beyond the diaphragm 240 allowing for organs (e.g., heart tissue) to be treated without entering the thoracic cavity. In one example, the ultrasound-device 254 may use high frequency ultrasound (commonly referred to as HIFU) to treat structures through the diaphragm. In one variation, the HIFU device has an active surface of several transducers arranged in a phased array which are capable of radiating focused therapeutic ultrasound energy at a fixed distance. The transducer itself may alternatively be capable of providing the focused ultrasound without requiring several transducers operating together.

In one variation, the ultrasound device 254 may contact the diaphragm adjacent to the right and left ventricles. The surgeon may then localize lesions and ablate tissue in the heart by transmitting ultrasound through the HIFU probe without having to penetrate into the thoracic cavity. In an additional variation, the ultrasound device 254 will incorporate a vacuum coupling and covering capable of forming a fluid tight seal with the diaphragm and use suction to engage the HIFU probe against the diaphragm thereby ensuring transmission of HIFU to the cardiac tissue without having interference of air or bone. Additional information regarding HIFU may be found on www.ushifu.com or www.internationalhifu.com.

FIG. 4B illustrates another variation of a diaphragm-approach for treatment of tissue structures within the thoracic cavity. In this variation, the access device 182 is used to dissect the esophagus 220 from esophageal vessels 221. As described in an example below, once the vessels 221 are sufficiently dissected from the esophagus, the access device may create a temporary cavity on a surface of the esophagus 220 by moving it away from the vessels 221.

In another variation of the method, the ultrasound-device 254 may be used to generate an image of perfusion patterns in the ventricles. The surgeon may use this imaging to identify slow conduction zones on the border of infarcted tissue. Such an approach may be used to treat ventricular tachycardia by mapping the perfusion flow patterns through the ventricular tissue and destroy those areas of tissue thought to cause the tachycardia. Regions responsible for inducing or maintaining ventricular tachyarrhythmias have been demonstrated to frequently occur in regions of slow and interspersed perfusion that can be delineated from completely infarcted tissue or viable tissue. Once these regions are identified, the high frequency ultrasound or any other energy modality and implementation design capable of focusing energy into local areas spaced at known distances from the ablation device (in this case targeting tissue in the ventricles from the diaphragm) are used to ablate the imaged slow or interspersed perfusion patterns and eliminate potential substrates of ventricular tachycardias.

Direct visualization of the posterior heart surface (or the esophagus or the lung) provides the surgeon with confidence when manipulating instruments along the cavity between the heart and lungs, and the spine and esophagus. An additional benefit of the DEPA process and associated devices is the ease of deployment due to the direct line to the posterior surface of the anatomy and the rapid healing post-procedure due to the absence of or limited deflation or other manipulation of the lungs when manipulating instruments along the posterior heart, the esophagus, or the posterior lung surfaces. The small incisions used to access the posterior heart surface during the DEPA process accelerates the healing process and reduces the visible scar.

The invention contemplates use of any surgical device that may be advanced through the access device to perform any procedure that benefits from or requires posterior visualization of organs as described herein. The integrated vacuum coagulation probe embodiments in co-pending U.S. patent application Ser. No. 11/208,465, Ser. No. 10/425,251, and U.S. Pat. No. 6,893,442 disclosed herein provide examples of devices that allow intimate contact specifically between a soft tissue surface and the energy portion of the device. In those example, the electrode(s) used to transmit energy (radiofrequency or ultrasonic) is capable of heating the soft tissue until achieving irreversible injury making the soft tissue non-viable and unable to propagate electrical impulses, mutate, or reproduce. These integrated vacuum coagulation probe embodiments may be utilized during the DEPA process of the invention to coagulate soft tissue capable of treating atrial fibrillation, ventricular tachycardia or other arrhythmia substrate, or eliminating cancer in lung, or other soft thoracic tissue by destroying target cells.

In addition, these integrated vacuum coagulation devices may be used to heat soft tissue along the posterior heart surface resulting in heat-induced contraction of collagen in such tissue thereby resulting shrinking of said soft tissue. For example, heating the mitral valve annulus along the posterior atrio-ventricular groove may induce shrinking of the annulus thereby correcting mitral valve regurgitation. However, it is understood that the invention is not limited to the above described vacuum coagulation probes. Instead, any number of coagulation, ablation, or surgical devices may be used as required.

The DEPA process and associated devices provide direct access to the posterior surface of the heart or lungs, or the esophagus, ascending or descending aorta, pulmonary artery, or other soft tissue structure, and enable manipulation of tissue structures to complete the desired surgical procedure. For example, the DEPA process facilitates accessing and visualizing the posterior left and right atria when creating lesions of structurally strong but electrically non-viable tissue along the atria to treat atrial fibrillation, atrial flutter, or other supraventricular tachycardia, or along the ventricles to treat ventricular tachycardia. In addition, such devices and methods could simplify and improve other soft tissue coagulation procedures by ensuring direct visualization while precisely and effectively heating a region of soft tissue. For example, ablation of cancer tissue in the lung or other anatomic structure is improved by the DEPA process and device embodiments of the invention. Similarly, the DEPA enables instrument manipulation and visualization for other cardiac (or non-cardiac) procedures that required accessing the posterior heart (or posterior lung or other anatomy between the posterior heart/lungs and the spine). For example, DEPA process will facilitate mitral valve compression procedures that involve placing patches or other compressive mechanism along the posterior mitral valve annulus adjacent to the posterior commisseur that is commonly associated with deformation due to ischemic injury or other cause of mitral regurgitation. For example, such treatment procedures as those described in pending U.S. application Ser. No. 10/269,844 entitled "Systems for Heart Treatment" may benefit from the DEPA process and devices because it enables direct access to the posterior surface of the heart and the target anatomic structures.

The DEPA process and device embodiments also enable reliable and controlled coagulation of soft tissue during less invasive procedures. Electrode(s) or antennas transmit energy (radiofrequency, direct current, ultrasonic, laser, infrared, or microwave) into tissue to cause the targeted soft tissue to heat thereby causing cellular responses that result in inhibiting conduction of electrical stimuli through the tissue cells but maintaining structural strength of the soft tissue. Alternatively, a cryogenic mechanism may be used to cool tissue below the isotherm of irreversible conduction block thereby rendering the tissue non-functional but structurally viable.

DEPA process embodiments and associated devices of the invention as applied to treating atrial fibrillation are described as an augmentation to other surgical access or as a stand alone surgical access. The DEPA process and associated devices of the invention may be used to augment other surgical access (e.g. thoracostomy, subxyphoid, mini-sternotomy, etc.) or may replace all other surgical access and provide the sole access for performing the surgical procedure.

Example of a Diaphragm Entry for Posterior Access (DEPA) Augmenting Other Surgical Access:

The example described below combines the DEPA process and associated devices with conventional or modified thoracoscopic access to ensure optimal visualization throughout the atrial fibrillation treatment procedure. It should be noted that the following description entails a thorough description of a particular DEPA approach in using an embodiment of a coagulation probe as described above and incorporated by reference. However, the inventive method may involve fewer, additional, or variations of the detailed steps to perform any particular surgical procedure. Furthermore, the treatment may be applied with any conventional device using any mode of treatment. Any such variations from the steps described below are contemplated to be within the scope of the invention.

Figure 5A:
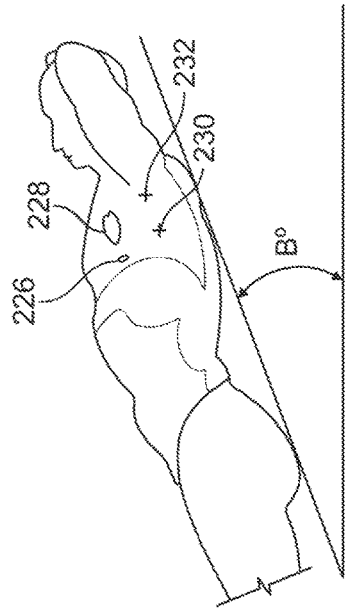
FIGS. 5A to 5C show side views of a patient with three processes of accessing the thoracic cavity to manipulate coagulation, dissection, and visualization devices.

In a standard procedure, the patient is prepared for the operation in a standard manner as described below:

The patient is taken to the operating room and placed in a supine position with the arms adductive and flexed at the elbows to expose both axilla, as shown in FIG. 5A. The patient's legs may be placed in stirrups similar to the technique described for Lap Nissen fundoplication, which allows the surgeon to stand between the patient's legs and operate. However, this patient placement is an illustrated embodiment and not mandatory to the technique. The patient is positioned so that maximum exposure is obtained to the lateral aspects of the chest wall from the waistline to the axilla. This may be facilitated by use of an operating table that narrows along the thoracic area to expose more of the sides of the patient's thoracic cavity and enables rotation of the patient along the thoracic cavity. The patient's lower extremities may be strapped across the waist and the legs within the stirrups to provide security to the bed. The upper thorax, arms, neck, and head may be secured to the bed to prevent the patient from slipping or sliding during extreme Trendelenburg (to angle A) as shown in FIG. 5A and extreme rotation to the left and right. A specialized operating table may be configured to provide the restraint, freedom of movement (from angle A (e.g. 30°) in FIG. 5A to angle B (e.g 30°) in FIG. 5B), and exposure described above.

The patient is intubated with an endotracheal tube; the bronchial lumen of the double lumen endotracheal tube is placed in the left main stem bronchus to facilitate individual inflation/deflation of the right and left lung lobes. Arterial monitoring is obtained via a radial artery and a Swan Ganz catheter is positioned via the right or left internal jugular for hemodynamic monitoring throughout the procedure. A transesophageal echocardiogram is used to visualize the heart and investigate function and the presence of thrombus. The stomach is emptied by the nasal gastric tube, and a foley catheter is inserted to drain the bladder.

Next, the patient is shaved from the waist to the axilla, and from left edge of the table to the right edge of the table. The patient is then prepped and draped to expose the clavicle to the waistline and to both sides of the bed for maximum exposure of the thorax, and abdominal cavity.

At this point, the left lung may be deflated by closing the endotracheal tube lumen feeding the left lung while the patient undergoes single right lung ventilation.

Figure 5B:
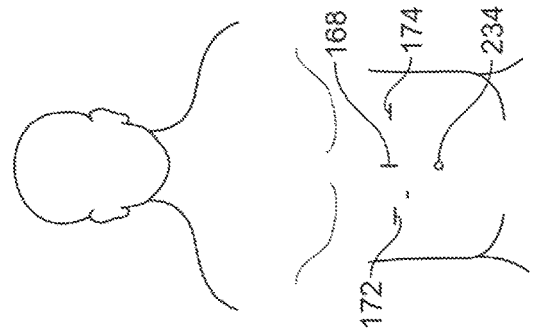

As shown in FIGS. 5A and 5B, thoracoscopy is performed by making a small incision 226 in the axillary line just beneath the left nipple at the 7th intercostals space for placement of a thoracoscope. A 2nd incision 228 is made anterior of the latissimus muscle in the mid-axillary line for retraction. A 3rd incision 230 is made more inferiorly and posteriorly to the latissimus muscle in the mid-axillary line. An additional incision 232 may be necessary anteriorly along the 4th or 5th intercostals space beneath the left pectoralis muscle, perhaps in the mammary crease. These incisions are placed after exposure of the heart is attained.

After placing the initial port and obtaining thoracostomy access, and allowing the left lung to deflate, attention is turned to the abdomen where various needles are used to insufflate the abdomen. After adequate insufflation, a vertical skin incision 168 is made in the mid-line approximately 3 to 7 cm below the xyphoid process, on the abdomen side of the diaphragm, as shown in FIG. 5D. This incision site is significantly below (e.g. at least 3 to 7 cm below) any incision used for previously disclosed sternotomy, thoracotomy, or subxyphoid access into the thoracic cavity, all of which are located on the thoracic side of the diaphragm.

The abdomen and its contents are visualized through the incisions. As shown in FIG. 5D, an additional incision 172 is made approximately 5 mm in size beneath the right subcostal area with a 3rd incision 174 of the abdomen being made in the same area on the left subcostal area. Through these two incisions, the left lobe of the liver is liberated from the diaphragmatic surface. As shown in FIG. 5D, an additional 5 mm port 234 is placed below the vertical incision to assist in retracting the left hepatic of liver away from the mid-line diaphragmatic area. It should be noted that those incisions may alternatively be used for liver procedures involving coagulating and/or resecting liver tissue to eliminate cancer or for other abdominal procedures involving coagulating and/or resecting cancerous tissue.

Once the diaphragm is adequately exposed, the diaphragm is grasped on both sides with Babcock clamps and a vertical incision is made in the mid-line of the diaphragm 3 cm anterior to the crus. This incision is extended thru the diaphragm until the pericardium is identified. It should be noted that this incision places the operator directly beneath the posterior surface of the heart providing direct access to the posterior atria. Once the pericardium is identified, it is grasped with endoscopic Babcock clamps and opened sharply with scissors. The pericardium opening is then continued allowing pericardial fluid to clear into the abdomen; this fluid is aspirated with suction.

Next, the surgeon performs the DEPA procedure. As described above with regards to FIGS. 1A-3F, the access device 182 is inserted through the abdomen and diaphragm and within the thoracic cavity. Creation of the temporary cavity exposes the posterior surface of the organ (in this case, the heart).

Once adequate exposure to the posterior surface of the heart is obtained, attention is turned to the left pericardium where the pericardium is opened with forceps, and scissors thoracoscopically through the left chest. A pericardial incision is made posteriorly beneath the left phrenic nerve along the anterior border of the left inferior pulmonary vein toward the superior pulmonary vein. Traction suture is placed in the pericardium and the pericardium is retracted anteriorly. A second retraction suture is placed posteriorly and retracted inferiorly to allow adequate exposure to the left inferior pulmonary vein region. The anterior pericardium is divided toward the left superior pulmonary vein to allow identification of the groove between the left superior pulmonary vein and the pulmonary artery. It should be noted that the pericardial incision can be made anterior to the phrenic nerve and extended inferiorly along the border of the phrenic nerve or the phrenic nerve can be isolated and liberated between the two incisions, one anterior and one posterior to the phrenic nerve leaving the phrenic nerve intact yet bridged between the diaphragm inlet of the super-most portion of the phrenic nerve and the thorax.

The exposure of the left atrial appendage may be obtained via an incision anterior to the left phrenic nerve more superiorly upon the pericardium. After exposure to the left superior pulmonary vein is achieved, a right angle and sharp scissors are used to dissect the pulmonary vein and left upper lobe of the lung is liberated to allow the left lung to fall into the left chest. Elevation of the patient in reversed Trendelenburg may assist in dropping the lung more inferiorly allowing better exposure of the pulmonary veins in this area. After adequate dissection is performed, the right angle is passed over the left superior pulmonary vein and is visualized with the diaphragm accessed pericardial endoscope. Once the right angle is viewed with the diaphragm accessed scope, an umbilical tape (or vessel loop, or other atraumatic elongate tether) is grasped using the pericardial grasping device through the separator/elevator central tube. This allows attachment of the coagulation device to this umbilical tape (or vessel loop, or other atraumatic elongate tether). It also allows traction on the pulmonary vein to position the coagulation device in a more appropriate location along the pulmonary vein.

The coagulation device is then advanced from behind and inferior to the left inferior pulmonary vein by attaching the device to the umbilical tape to above the left superior pulmonary vein. The device is then pulled and visualized with the DEPA scope to be in the appropriate position behind the pulmonary veins. Once the coagulation device is appropriately positioned from inferior and posterior to the left inferior pulmonary vein to the left superior pulmonary vein but in the posterior pericardium, the coagulation device is placed into contact (e.g. via vacuum application for the vacuum integrated devices referenced above) with the left atrium. This position is directly viewed with the DEPA scope prior to transmitting the energy through the coagulation device and into soft tissue.

The coagulation device is further retracted along the superior pulmonary vein and anterior to complete the top of the superior pulmonary vein coagulation. Once visualization is verified by the DEPA scope, the coagulation is performed. At this point, the completion of the pulmonary vein isolation is performed by completing the anterior coagulation line using the thorascope to visualize the appropriate position of the coagulation device and confirm tissue contact with the coagulation mechanism.

At this point, a coagulation line is created toward the left atrial appendage from the pulmonary vein coagulation lines taking care not to damage the phrenic nerve. This position is performed by direct visualization with the thorascope. Once this coagulation line is completed via the left thorax, attention is turned to the left atrial appendage.

Figure 17A:
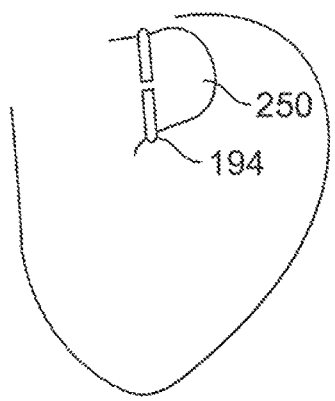
FIGS. 17A to 17C show side views of an atrial appendage closed during a Diaphragm Entry for Posterior Access process.
Figure 17B:
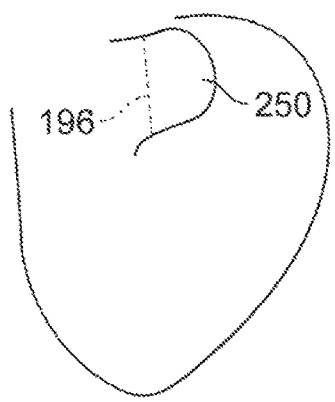
Figure 17C:
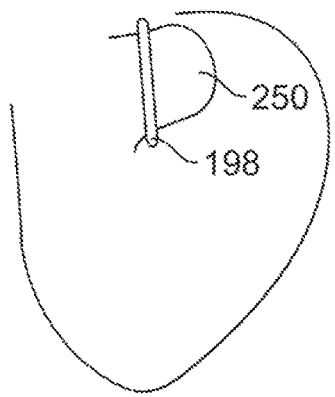

An appendage grasper can be used to grasp the tip of the atrial appendage for retraction. FIGS. 16A-16D show an example of an appendage grasper 200. The appendage closure mechanism, as shown in FIGS. 17A to 17C is applied under direct visualization from the thorascope. Staples 194, clips 196, clamp 198, sutures, or other mechanism may be applied to close the left atrial appendage 250. If staples, clips, or sutures are used, pericardium may be incorporated into the closure site to prevent bleeding.

The umbilical tape is then repositioned across the top of the left superior pulmonary vein and remains within the pericardium as far to the right as possible. The left lung is reinflated leaving the umbilical tape posterior towards the right superior pulmonary vein. The right lung is then allowed to deflate fully using similar thorascope ports and position as the left, described above.

A right thoracoscopy is performed, as shown in FIG. 1A, and again the pericardium is liberated anteriorly to the phrenic nerve to allow exposure of the right inferior pulmonary vein, the space between the inferior vena cava and the right inferior pulmonary vein. The right pulmonary vein is liberated from the pulmonary artery and the superior portion right of the right superior pulmonary vein. Once this separation is visualized, the right angle is visualized to be within the pericardium by the DEPA scope. Again, umbilical tape is positioned in this area and grasped by the DEPA grasping instrument. The umbilical tape is placed towards the right inferior pulmonary vein. The coagulation device is positioned from inferiorly along the posterior right pulmonary vein along the left atrium. Traction with the umbilical tape assists with positioning the device posteriorly. Once the coagulation device is positioned, it is actuated to coagulate a line of soft tissue. Again the right pulmonary veins are coagulated in a similar fashion to the left pulmonary veins described above, using assistance of the umbilical tape. The anterior line along the right pulmonary veins is performed under direct visualization from the right thorascope. Additional exposure of the intra-atrial groove, separating the right atrium from the pericardium, may provide better positioning of the coagulation device. Once the device is positioned along the right pulmonary veins, the coagulation device is activated and the right pulmonary vein isolation is completed.

At this point, the umbilical tape that remained placed in the left pulmonary veins is grasped from above the superior pulmonary veins using the DEPA scope to assist this position. The umbilical tape is pulled into the right chest from the left chest and is attached to the coagulation device. The coagulation device is positioned along the posterior left atrium. Positioning of the coagulation device is conducted under direct visualization from the DEPA scope. After position is confirmed, the coagulation device is activated creating a line of coagulated tissue.

It should be noted that rotation of the patient left and right, as well as Trendelenburg or reverse Trendelenburg may be beneficial to appropriately position the heart for maximum exposure of the DEPA scope. The access device 168 may require asymmetric expansion to further rotate the heart relative to the patient, depending on the patient's body, anatomy orientation, and table configuration.

After creating all desired left atrial coagulation lines, the coagulation device is positioned from behind the inferior vena cava using the DEPA scope and along the anterior-most portion of right atrium and is connected to the right pulmonary vein isolation coagulation line. Once positioned, the coagulation device is activated. This coagulation line continues around the medial portion of the inferior vena cava toward the coronary sinus. Coagulation is performed to the atrio-ventricular groove in this area with care to protect the right coronary artery. The coagulation is performed to the coronary sinus taking care to remain posterior to the coronary sinus and avoiding the AV node.

After creating the right atrial coagulation lines, attention is then turned back to the left atrium, where a coagulation line is created from the inferior pulmonary vein to the coronary sinus towards the mitral valve P3 leaflet. Care is taken to protect the coronary sinus and circumflex once position is confirmed and coagulation activated.

Figure 6A:
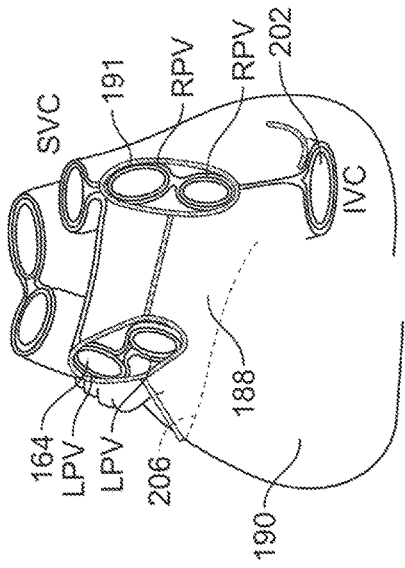
FIGS. 6A to 6D show a perspective view of the posterior heart with lesions created via a Diaphragm Entry for Posterior Access process embodiment of the invention.

FIG. 6A shows the completed coagulation line 191. After completion the coagulation device is removed, the DEPA scope is removed, the expandable member on the access device 168 compresses into a low profile allowing for retraction of the access device 168. A smooth mesh patch (having a width and length of approximately 3 cm×3 cm) is used to cover the diaphragm incision and is stapled or sutured to the diaphragm. Once the diaphragm incision is repaired, the left lobe of the liver is released and the abdomen deflated. Both lungs are fully inflated. If no parenchymal injury to the lungs is observed, no chest tube is necessary. If parenchymal injury is noted, chest tubes are placed bilaterally with Heimlich valves and the patient is returned to a more upright reversed Trendelenburg position and both lungs are reinflated with suction on both catheters. Once this is performed, as long as there is not injury to the lung, the chest tubes are removed on full ventilation by Valsalva, to prevent air space in the left or right pleural spaces. The incision in the abdomen is closed in two layers, as are the thorascopic incisions.

Example of a Stand Alone Diaphragm Entry for Posterior Access (DEPA):

This embodiment describes a stand alone DEPA process that does not require additional surgical access through the thoracic cavity, and associated devices with during atrial fibrillation treatment procedures. Again, it should be noted that the following description entails a thorough description of this particular DEPA approach using an embodiment of a coagulation probe as described above and incorporated by reference. However, the inventive method may involve fewer, additional, or variations of the detailed steps to perform any particular surgical procedure. Any such variations from the steps below are contemplated to be within the scope of the invention.

As stated above, the patient is prepped and intubated. The endotracheal tube may enable individual inflation and deflation of lung lobes; however the stand alone DEPA process may not require deflation or retraction of lungs due to the access location which comes up through the diaphragm directly adjacent the posterior left atrium and left ventricle. Elimination of the need to deflate or retract the lungs (not attainable with conventional surgical approaches) will provide a substantial benefit to patients by preventing lung damage and expediting patient recovery.

As stated above, hemodynamic monitoring is performed throughout the procedure, and TEE is used to visualize the heart and investigate function and the presence of thrombus. The stomach is emptied by the nasal gastric tube, and a Foley catheter is inserted to drain the bladder. Various needles are inserted into the abdomen to insufflate the abdomen. After adequate insufflation, a vertical skin incision is made in the mid-line approximately 3 to 7 cm below the xyphoid process, on the abdomen side of the diaphragm, as shown in FIG. 5D. This incision site is significantly below any incision used for previously described subxyphoid access into the thoracic cavity, which have been located on the thoracic side of the diaphragm.

The abdomen and its contents are visualized through the incisions. An additional incision is made approximately 5 mm in size beneath the right subcostal area with a 3rd incision of the abdomen being made in the same area on the left, as shown in FIG. 5D. Through these two incisions, the left lobe of the liver is liberated from the diaphragmatic surface. As shown in FIG. 5D, an additional 5 mm port is placed in the right subcostal area to retract the left hepatic of liver away from the mid-line diaphragmatic area. Once the diaphragm is adequately exposed, the diaphragm is grasped on both sides with Babcock clamps and a vertical incision is made in the mid-line of the diaphragm 3 cm anterior to the crus, until the pericardium is identified. Once the pericardium is identified, it is grasped with endoscopic clamps and opened.

Next, the surgeon performs the DEPA procedure. As described above with regards to FIGS. 1A-3F, the access device 182 is inserted through the abdomen and diaphragm and within the thoracic cavity. Creation of the temporary cavity exposes the posterior surface of the organ (in this case, the heart).

Once adequate exposure to the posterior surface of the heart is obtained, the pericardial reflections may be dissected at regions 224, if necessary, as shown in FIGS. 13A and 13B to free the pulmonary veins 164 and/or inferior vena cava 202 to allow an access device 182 to further define the cavity between the posterior heart surface and the spine. A maneuverable dissector 124, as shown in FIGS. 13A, 13B, 14A and 14B, may be used to dissect the pericardial reflections or other interconnective tissue or fat. This dissector can be steered remotely to change the axis of the dissecting clamp relative to the separator/elevator thereby facilitating access of target tissue located off axis from the separator/elevator central lumen/opening. It should be noted that the central lumen 186 of the access device 182 may alternatively comprise an elliptical cross-section, as shown herein, such that rigid instruments can be rotated off axis and access the pericardial reflections without the need for remote steering in the dissector.

It should also be noted that this posterior access through the pericardium obviates the need to manipulate or avoid the phrenic nerves, which run along the anterior heart surface. The pericardial incision is made to fully expose the posterior left atrium and enable rotation of the heart via manipulation with the separator/elevator, rotating the patient, placing the patient in Trendelenburg or reverse Trendelenburg, or other technique. Traction sutures may be placed in the pericardium adjacent to the pericardial incision to further manipulate the heart.

After adequate dissection of the pericardial reflections is performed (if needed), a grasping device (e.g. clamp (deflectable or fixed), snare (deflectable or fixed), or preshaped clamp) is inserted through the separator/elevator central lumen or opening and is passed along the left pulmonary veins under direct visualization from the DEPA scope. A silastic tube, an umbilical tape, or other atraumatic tensile member 248 is advanced around the left pulmonary veins 164 using the grasping device 192, and is temporarily engaged to the coagulation device 2 to retract the coagulation device into position, as shown in FIG. 13C.

The coagulation device is then advanced partially or fully around the left pulmonary veins by advancing the coagulation device and/or retracting the umbilical tape. The position and engagement of the coagulation device is continuously visualized with the DEPA scope 184. Once the coagulation device is appropriately positioned partially or fully around the left pulmonary veins, the coagulation device is placed into contact (e.g. via vacuum application for the vacuum integrated devices referenced above) with the left atrium. This position is directly viewed with the DEPA scope prior to transmitting the energy through the coagulation device and into soft tissue.

Figure 6B:
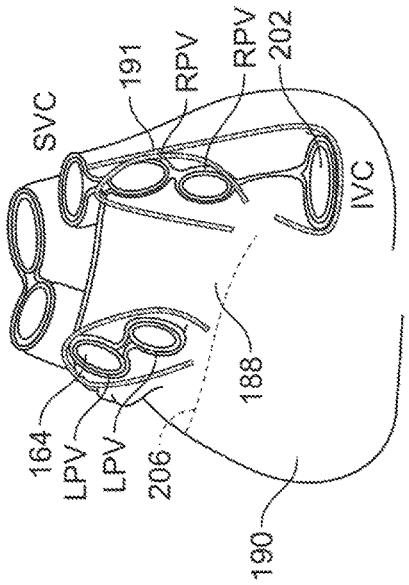

After creating the first coagulation line, the coagulation device is further retracted along the left pulmonary veins to complete the isolating coagulation line, as shown in FIG. 6B. Once visualization is verified by the DEPA scope, the coagulation is performed. At this point, the completion of the left pulmonary vein isolation is confirmed using pacing techniques that demonstrate conduction block from the left pulmonary veins to the rest of the atria.

A coagulation line is then created along the left atrial appendage from the left pulmonary vein coagulation line to the mitral valve annulus 206 at the location where the great vein and circumflex have branched away from the annulus exposing a segment of annulus along which no coronary vessels run, as shown in FIG. 6B. This position is performed by direct visualization with the DEPA scope. Once this coagulation line is completed, the left atrial appendage is closed. The appendage grasper 200, shown in FIGS. 16A to 16D is used to grasp the atrial appendage and the atrial appendage is retracted. The appendage closure mechanism is applied under direct visualization from the DEPA scope. Staples 194, clips 196, clamp 198, sutures, or other mechanism may be applied to close the left atrial appendage, as shown in FIGS. 17A to 17C. If staples, clips, or sutures are used, pericardium may be incorporated into the closure site to prevent bleeding.

The coagulation device is then repositioned around the right pulmonary veins using the grasping mechanism described above and umbilical tape. It should be noted that the coagulation device may alternatively incorporate a preformed shape or steering mechanism that facilitates advancing and deflecting the coagulation mechanism along the posterior atria. The coagulation device is positioned, under direct visualization from the DEPA scope, around the right pulmonary veins and activated in serial steps that form lesion lines that intersect to form a complete lesion absent of gaps at the intersection(s).

After creating the right pulmonary vein coagulation lines, the coagulation device is positioned along the posterior left atrium 188 to intersect the left pulmonary vein and right pulmonary vein coagulation lines 191, as shown in FIG. 6B. Positioning of the coagulation device is again conducted under direct visualization from the DEPA scope. After position is confirmed, the coagulation device is activated creating a line of coagulated tissue.

It should be noted that rotation of the patient left and right, as well as Trendelenburg or reverse Trendelenburg may be beneficial to appropriately position the heart for maximum exposure of the DEPA scope. The separator/elevator may also incorporate asymmetric expansion to further rotate the heart (side-side, head-toe, or other planar relationship) relative to the patient, depending on the patient's body, anatomy orientation, and table configuration.

After creating all desired left atrial coagulation lines, the coagulation device is manipulated through the working channel of the access device or opening under the inferior vena cava to create a coagulation line from the inferior vena cava to the tricuspid annulus under the eustacian ridge. Once positioned, the coagulation device is activated. Alternatively or in addition a coagulation line may be extended from the inferior vena cava 202 to the coronary sinus as shown in FIG. 6B taking care to remain posterior to the coronary sinus and avoiding the AV node.

Once all coagulation lines are completed, as shown in FIG. 6B, the coagulation device is removed, the grasping instruments are removed, the DEPA scope is removed, and the access device is compressed into a low profile and retracted. A smooth mesh patch is used to cover the diaphragm incision and is stapled or sutured to the diaphragm. Alternatively, suture may be placed along the diaphragm to close the diaphragm incision without the need for a mesh patch. Once the diaphragm incision is repaired, the left lobe of the liver is released and the abdomen deflated. Since the lungs have not been deflated, parenchymal injury to the lungs is avoided. The incision in the abdomen is closed in two layers.

Example of an Esophageal Dissection.

Once a patient is identified and prepared for the procedure, a small skin incision is made at the umbilicus and the abdomen is inflated appropriately with a laparoscope. After obtaining adequate inflation, an endoscope is inserted and an additional abdominal port incision is made in the right subcostal area to retract the left lobe of the liver superiorly to allow exposure of the esophageal hiatus. Two separate abdominal port incisions are made just inferior to the left and right costal margins to provide adequate mobilization and placement of the dissecting tools. The stomach and the gastric epiploic artery was carefully protected and the short gastric was divided. The gastric epiploic is protected so the gastric epiploic artery can be identified. The short gastric is identified and freed toward the spleen using a Harmonic Scalpel. Once the stomach is completely liberated and the right gastric epiploic artery is completely protected, the dissection is continued to the esophageal hiatus at the crus of the diaphragm. Attention is then turned to the first and second portion of the duodenum where dissection was performed laparoscopicly to mobilize the duodenum off the right kidney. The stomach is further mobilized. The dissection is extended toward the right crus of the diaphragm identifying the left gastric artery. The left gastric artery is carefully divided using endoscopic stapling and hemostasis is verified. The endoscopic pyloroplasty is performed using and endoscopic stapling device to applicate the duodenum over the pyloric and an anatomosis is created to prevent gastric outlet obstruction.

At this point, using endoscopic Harmonic Scalpel, the esophagus is further liberated within the mediastinum. This dissection is continued as far as one could see with the laparoscope and the Harmonic Scalpel thru the laparoscopic incision in the midline. The access device is then placed into the thoracic cavity and an endoscope is positioned through the access device and into the posterior mediastinum anterior to the esophagus. Using a dissector, the esophageal vessels are clearly identified. The vessels are then divided using a Harmonic Scalpel. Once the esophagus is liberated completely toward the mediastinum, the access device is placed behind the esophagus and in singular fashion, the lateral esophageal vessels are divided from the esophagus. It is preferable to visualize the esophagus to confirm that it is free of all attachments.

Examples of Lesions

It should be noted that any pattern of curvilinear, transmural lesions may be created along the epicardial surface or the endocardial surface with the coagulation devices using the DEPA process in conjunction with another surgical access or as a stand alone process.

One potential left atrial lesion pattern involves creating a "C" that passes from the mitral valve annulus 206 adjacent the left atrial appendage (where the great vein and the circumflex do not parallel the atrioventricular annulus but have curved towards the apex of the left ventricle) above the superior pulmonary vein and back towards the mitral valve annulus adjacent the right pulmonary veins; or below the inferior pulmonary veins and towards the anterior mitral valve annulus. Another left atrial lesion pattern involves creating a "V" where the intersection resides at the mitral valve annulus adjacent to the left atrial appendage and each segment passes on opposite sides of the pulmonary veins and ends adjacent to the interatrial septum. A stretched "B" with each curved segment extending around either the left pulmonary veins or the right pulmonary veins and the central links separated by a distance wherein the top line of the "B" connects to the mitral valve annulus adjacent the left atrial appendage may also be created.

Figure 6C:
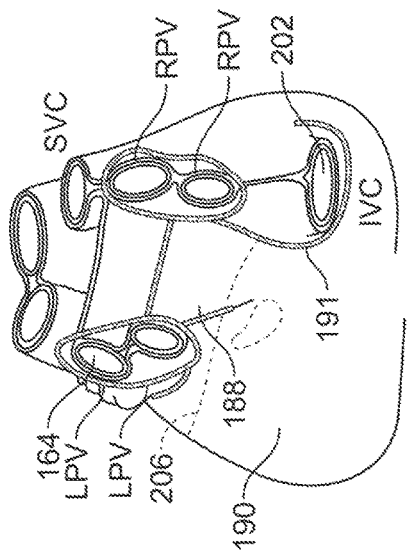
Figure 6D:
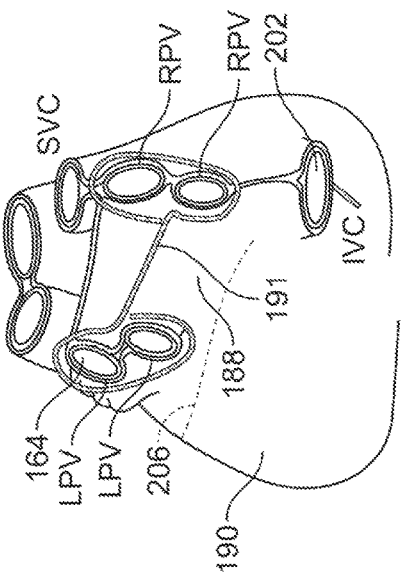

As shown in FIG. 6C, a stretched "S", reverse "S", or figure eight coagulation line 191 with the initiating point occurring at the mitral valve annulus adjacent to the left atrial appendage and curving from that base point encompasses the left and right pulmonary veins as pairs within the curved segments. As shown in FIG. 6D, two "C" lesions 191, one extending around the left pulmonary veins 164 and one extending around the right pulmonary veins 164, connect to the mitral valve annulus 206 and incorporate a flutter lesion extending from the inferior vena cava 202 to the tricuspid annulus. In addition to the various left atrial lesion patterns above, right atrial lesions may be created along the cristae terminalis, from the inferior vena cava to the superior vena cava, from the cristae terminalis to the tricuspic annulus, from the superior vena cava to the tricuspid annulus, or other geometry capable of preventing atrial flutter along the right atrium.

Other Posterior Access Embodiments

Figure 5C:
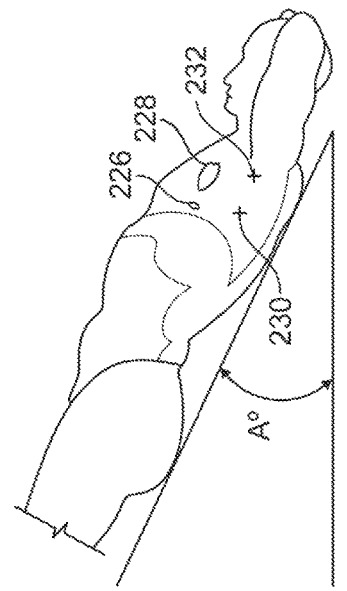
Figure 5D:
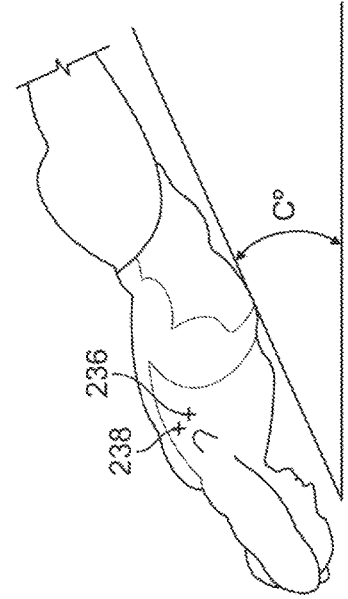
FIG. 5D shows a top view of a patient positioned on the operating table during a Diaphragm Entry for Posterior Access procedure of the invention.

FIG. 5C shows an alternative access that provides direct visualization and manipulation of the posterior heart surface or lungs. The patient is placed and restrained on his/her belly on the operating room table. As such, the patient's back is accessible by the surgeon. Gravity causes the heart, lungs and other anatomy to move away from the back providing space in which to access and manipulate instruments along the posterior heart or lungs. Two back incisions 236 and 238 are created away from the spine and trocars are placed to access the thoracic cavity from the back. The trocars are located adjacent the spine and away from the aorta and esophagus to provide direct access to the posterior heart and lungs.

Separator/Elevator Embodiments

FIGS. 7A to 7C show an example of a novel access device 182 for creating a temporary cavity within the body. FIGS. 7A-7C show, respectively, a top view, a side-sectional view, and an end view of an alternative access device 182. Generally, the device elevates organs and separates adjacent organs or tissue surfaces to create a surgical area within the body via creation of a temporary cavity. In the variation of FIGS. 7A-7C, the device 182 incorporates two expandable members 212. As described herein, the device 182 may include any number of expandable members 212. However, regardless of the number used, the expandable members 212 expand about the elongate member 210 (also referred to as a guide tube) to separate and elevate organs to create the temporary cavity.

In the variation shown in FIG. 7A, the expandable members comprise two balloon bladders 212 (or a single balloon can be secured to the top and bottom of the elongate member 212 to define two bladders). The balloons 212 are oriented along the two opposing sides of the elongate member 210. When the balloons 212 inflate, as shown in FIGS. 7A and 7C, they form a pillow-type support that fits around the spine and esophagus on one side and the heart on the other side. In this manner, the balloons 212 serve not only to separate the organs, but also to stabilize them. It should be noted that the separation of the balloons on the elongate member does not need to be symmetric, as shown in FIG. 7C but may be different depending upon the particular application. For example, a shorter balloon can be used along the side of the device 182 that contacts the heart and a longer balloon can be used on the side of the device 182 that contacts the spine and esophagus, or vice-versa, depending on the patient anatomy. The balloons may be fabricated from silicone, urethane, polyester, PET, polyurethane, nylon, PEBAX, or other polymer capable of enlarging in response to being exposed to an inflation media. The guide tube 210 can be fabricated from any polymer and preferably has enough rigidity to provide column strength needed when inserting the access device into the space between organs (e.g., the heart and the spine). For example, the guide tube can be fabricated from polyurethane, PTFE, FEP, polyester, or other material that can be extruded or molded into the desired shape.

In variations of the access device 182, the expandable members (e.g., balloons 212) expand in a non-uniform manner about the elongate member 210. For example, as shown in FIG. 7C, the balloon 212 expand away from the sides of the elongate member 210 more than they expand away from the top and bottom of the elongate member 210 This particular configuration permits creation of the temporary cavity without moving the organs to far from the opening 186 or slot 187 of the elongate member 210. Although variations of the access device 182 include expandable members that expand non-uniformly about the elongate member 210, the device includes variations where the expandable member expands in a uniform manner as well.

As shown in FIG. 7B, the elongate member 210 includes at least one inflation lumen 214 that is fluidly coupled to the interior of one or both balloons 212. Depending on the application, each balloon 212 may have an individual inflation lumen 214 to provide more control over inflation of the balloons and separation of the organs. The balloons may be inflated using saline, CO2, or other biocompatible fluid. The inflation lumens may be routed to the proximal end of the device including through ports in the handle. As discussed herein, the individual balloons may be inflated to different pressures and/or volumes such that one balloon provides more separation than the other. For example, when used against the heart, this mechanism causes the heart to rotate in one direction or the other providing a mode of manipulating the heart within the thoracic cavity. For example, this manipulation allows instruments to better access the lateral surfaces of the heart, and/or even the anterior surface of the heart.

FIG. 7C illustrates the elongate member 210 including one or more visualization elements 246. The visualization element may be an optic fiber, a CCD camera, a light source, etc. The optic fiber could be used to transmit light and illuminate the cavity defined by the access device 182. Alternatively, or in combination, the access device 182 may incorporate near-field infrared transducers to identify blood vessels (veins and arteries) during use. By incorporating such near-field infrared transducers, the surgeon can identify blood vessels (e.g. the pulmonary veins, coronary sinus, esophageal vessels, or other small vessels while getting to the heart or separating the esophagus) and avoid them while dissecting or localizing them. Such near-field infrared technology can visualize vessels 2 mm under the surface of tissue.

As shown in FIGS. 7A-7C, the device 182 includes a working channel 211 that permits delivery of surgical tools and/or scopes to the temporary cavity. This allows for creation of a surgical field at the temporary cavity. The working channel 211 terminates at the opening 186 at the distal end of the elongate member 210. Although FIGS. 7A-7C illustrate the opening 211 at a front face of the device 182, the opening 211 may be located at an end of the device 182 on a side as shown below.

The device 182 may also include a slot-type opening 187 on one or more sides of the elongate member 210. The slot 187 permits access to a larger portion of the organ within the temporary cavity. As shown, the ends of the balloons 212 extend beyond the slot 187 improving the ability of the device to form the temporary cavity. When the device is used against the heart, the slot provides access to the posterior heart surface located within the contact region between the access device and the heart. Without the slot 187, the access is only beyond the opening 186 of the elongate member 210.

As shown in FIGS. 7A-7C, variations of the access device 182 include elongate members 210 having non-circular cross sections (e.g., oval as shown). The non-circular cross section of the working channel 211 provides the ability to place multiple instruments through the access device 182. To further increase the ability of the device 182 to handle multiple tools, devices 182 of the present invention may be used with scopes having camera connections that are oriented at an angle (e.g. anywhere up to 90 degrees) from the scope shaft so the handles will not interfere with the scope camera.

In the examples shown in FIGS. 7A and 7B, a planar surface 245 on one side of the device 182 permits an increased surface area contact between the device and tissue when creating the temporary cavity. This increased surface contact provides additional stability of the device 182 when in use. Although, the expandable members 212 are shown to be placed on sides of the device 182 adjacent to the planar surface 245, additional variations of the device include expandable members on any surface/side of the device 182.

As shown, a proximal end or proximal portion of the access device 182 is adapted to allow manipulation of the access device from outside of the body. FIG. 7A illustrates proximal handles 256 that allow manipulation of the access device 182 and also prevents pushing the proximal end of the elongate member 210 or access device 182 completely into the patient.

As shown in FIGS. 7B and 7C, a malleable or shapeable support 244 may be incorporated into the elongate member 210 to allow shaping the member into a desired configuration. The shape is selected to improve the ability of the device to direct the scope and instruments towards the desired site of a temporary cavity (e.g., posterior region of the heart, or other anatomic structure). The support 244 may be placed in a support lumen such that the support 244 is slidable within the support lumen of the elongate member 210. Alternatively, or in combination, the elongate member 210 may be fabricated from a shapeable material. Accordingly, the elongate member 210 could be shaped to a desired profile.

FIG. 7C also illustrates the access device 182 as having an optional suction or aspiration lumen 262. Because the device is suited for creation of a temporary cavity to perform a surgical procedure under direct visualization, it will be important to keep the scope or visual element clear from bodily or other fluids. Accordingly, a suction device may be advanced through the working channel. Alternatively or in combination, a suction or aspiration lumen 262 may be placed within the elongate member 210.

Figure 7D:
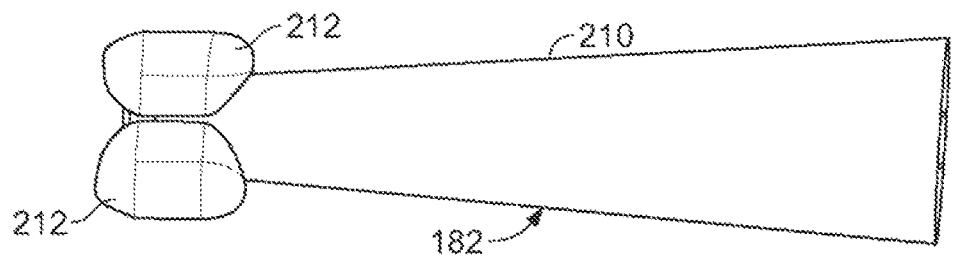
FIGS. 7D to 7E show another variation of an access device having a tapered elongate member.
Figure 7E:
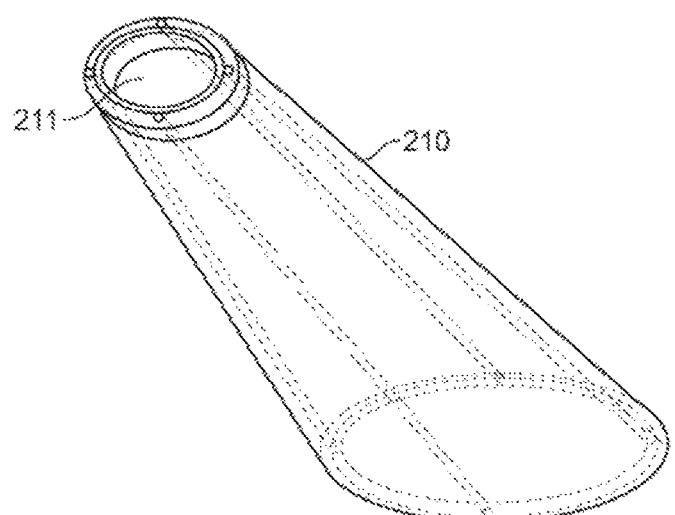

FIGS. 7D to 7E illustrate another variation of an access device 182. In this variation, the elongate member 210 is tapered from the proximal end the distal end. This tapering configuration allows the elongate member 210 itself to separate tissue as the device 182 advances to a target site. FIG. 7E illustrates a perspective profile of the tapered elongate member 210 (showing the various inflation and/or aspiration lumens). Again, the cross-sectional profile of the working channel 211 may be any geometric shape. However, shapes in which working channel width is not equal to the working channel height may be preferred (e.g., rectangular, oval, trapezoidal, etc.). FIG. 7C also demonstrates a variation of a device 182 where the expandable members 212 surround the distal end of the elongate member 210. This variation creates a space between the elongate member 210 and the organ.

Figure 7F:
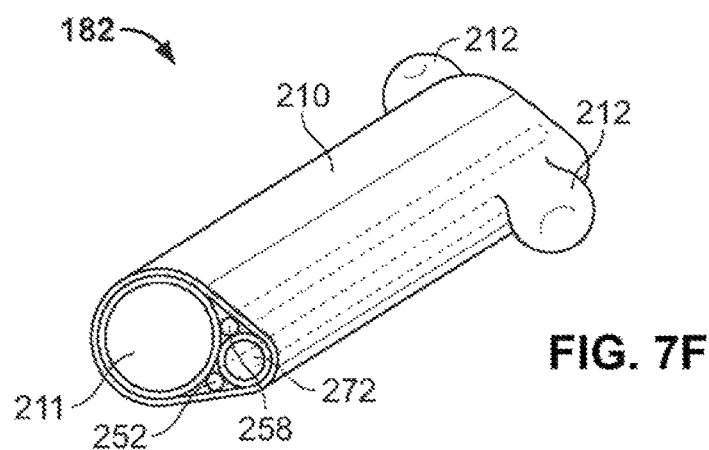
FIGS. 7F to 7I show variations of an access device having a working channel and a second working lumen.

FIGS. 7F to 7I illustrate additional variations of access devices 182. As shown in FIG. 7F, the access device 182 may include an additional working lumen 272 within the elongate member 210. The additional working lumen 272 in this variation is separate from the working channel 211 and provides an access channel that permits the ability to leave a device at the temporary cavity while advancing and/or removing other devices without causing undue interference between devices. For example, the additional working lumen 272 may be used to advance a scope-type device to the temporary cavity. In this manner, the scope-type device may be left in the working lumen 272 while other devices are inserted and manipulated in the working channel 211. This reduces the chance that the scope is disturbed.

Figure 7G:
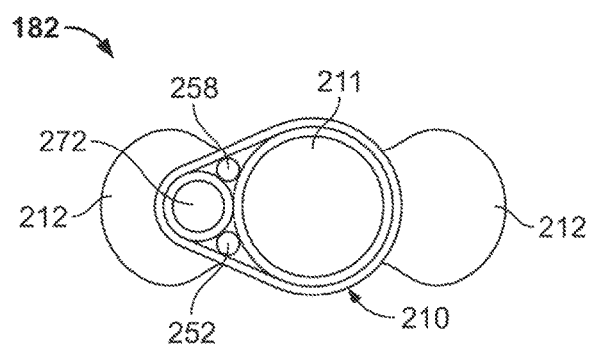

FIG. 7G illustrates a front view of the access device 182 of FIG. 7F. As shown, the access device 182 includes a working channel 211, an additional working lumen 272, an inflation lumen 258 coupled to the expandable members 212 and an aspiration lumen 252. In one variation, the multi-lumen access device 182 may be fabricated from a plurality of tubes having a covering or coating that defines the outer surface of the elongate member 210. As illustrated, the device 182 may include multiple expandable members 212 located at a distal end.

Figure 7H:
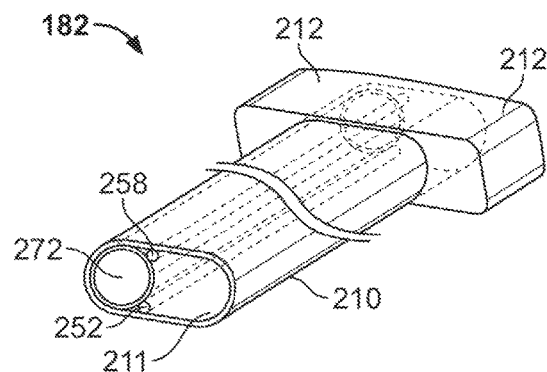
Figure 7I:
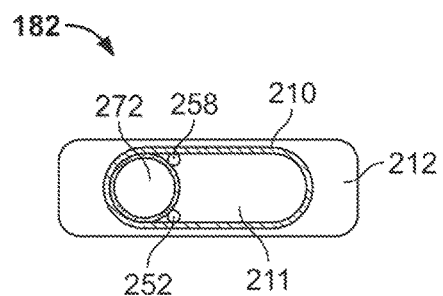

FIG. 7H illustrates another variation of an multi-lumen access device 182. As shown, the access device 182 may comprise an elongate member 210 having a passage to serve as the working channel 211. Separate tubes or similar structures may be placed within the working channel 211 to form a working lumen 272, aspiration 252, and inflation lumen 258. These lumens may also be formed using an extruded multi-lumen elongate member 210. FIG. 7I illustrates a rear view of the access device 182 of FIG. 7H. As shown, the expandable members 212 may be formed from a single balloon bladder located about the distal end of the device 182.

Figure 7J:
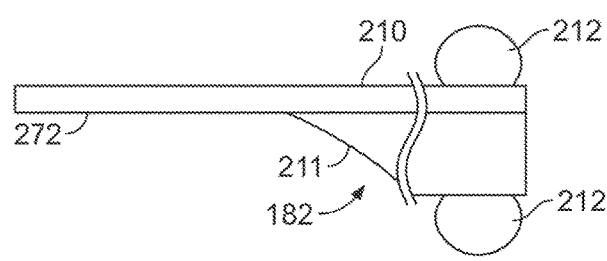
FIG. 7J show a variation of an access device where the working channel and second working lumen are offset at the proximal end of the device.

FIG. 7J show a variation of an access device 182 where the working channel 211 and second working lumen 272 are offset or staggered at the proximal end of the device 182. This configuration reduces interference between devices at the user end of the access device 182. Furthermore, the proximal end of the working channel 211 may be tapered along an end of the elongate member (as shown) to increase the area through which instrumentation enters the working channel 211.

FIGS. 8A to 8C show respective top, side, and bottom views of an access device 182 as described herein having both an expandable member 212 and separate stabilizers strands 216. As shown, the expandable member comprises a balloon 212 affixed to the elongate member 210 or guide tube. In this variation, the elongate member 210 has a non-circular cross-section defining a working channel 211 (e.g. elliptical, rectangular as shown, trapezoidal, or any other geometric shape). The working channel 211 allows for access to the temporary artificial cavity formed by the device. The elongate member 210 may be shapeable or have a particular curve as discussed herein. As noted above, in those variations where the guide tube maintains a curve, the curve will be selected depending on the desired surgical application. For example, to direct access from the skin incision/puncture on the abdominal side of the diaphragm, under the diaphragm and towards the posterior surface of the heart the access device 182 may have a distal portion that is curved or angled as shown in FIG. 8B.

In the variation shown in FIGS. 8A-8C, the balloon is affixed along a planar side of the elongate member 210 such that the sides and bottom of the balloon are free and not attached. This configuration allows the balloon 212 to adjust to the spine, esophagus, and other structures while separating the heart with the stabilizer side of the elongate member 210. The stabilizer strands 216 may be fabricated to be malleable so that they fit around an organ and stabilize the organ during the procedure. For example, when used against the heart, the strands stabilize the heart as the balloon inflates to create the temporary cavity. The stabilizers 216 support the heart during manipulations of the instruments along the posterior surface of the heart or within the artificial cavity defined by the access device 182.

The stabilizer strands 216 are preferably fabricated from the elongate member 210 by cutting slots and preshaping the stabilizing features. However, the stabilizer may alternatively be fabricated from another component (e.g. spring metal such as spring steel or nitinol) covered with an atraumatic polymer and secured to the guide tube.

Figure 9A:
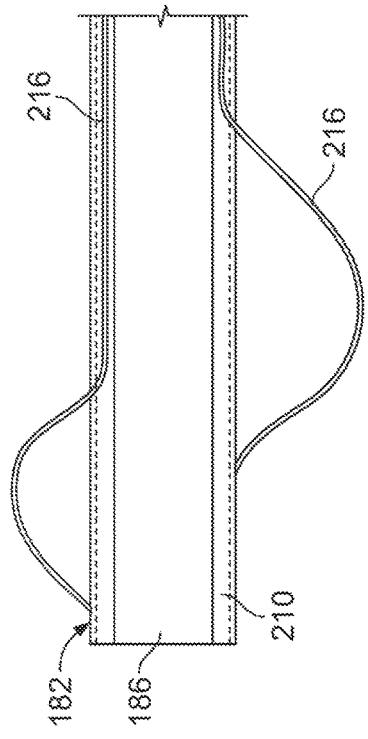
FIGS. 9A to 9D show front and side-sectional views of an access device using stabilizer members and stabilizer members within a balloon.
Figure 9B:
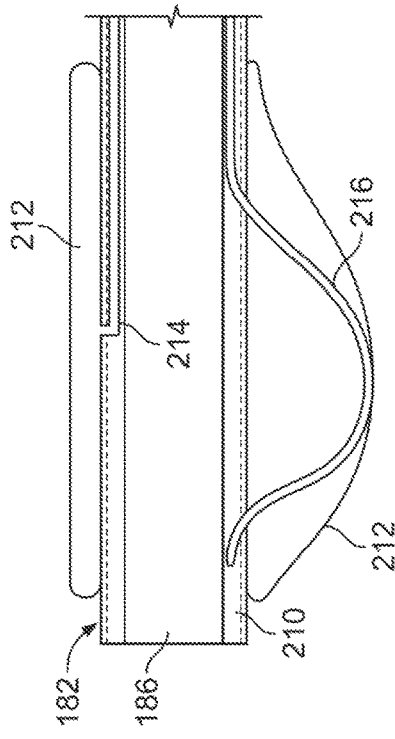

FIGS. 9A and 9B show an alternative access device 182 that incorporates expandable members comprising enlargeable strands 216 or stabilizers. The strands 216 may be preformed strands 216 or stabilizers fabricated from a spring material (e.g. a flexible polymer, spring stainless steel, nickel titanium, or other metal treated to meet the elastic requirements of the device). In some variations, the strands 216 assume a preshaped configuration upon deployment of the device. The strands 216 can be deformed during deployment to nest or separate the appropriate organ. The strands 216 may be malleable or resilient. For elastic or resilient strand configurations, the strands 216 have an expanded preshaped orientation. Wires may be used to retract the strands into a low profile. Once positioned, the wires may release the strands such that they expand radially outward into contact with the anatomy. In variations where the device is used to separate the heart from the esophagus, once both sets of strands are advanced, the strands separate the heart from the spine and esophagus, providing a temporary cavity in which instruments can be inserted and scopes can provide direct visualization, (e.g., as shown in FIGS. 3A to 3C).

In alternate variations, the strands 216 are actuated into an enlarged configuration upon positioning of the device. In the variation shown in FIG. 9B, the strands 216 can be actuated to cause advancement or retraction of the strands. As shown, one end of the strand may be affixed to the elongate member 210, while the other end may be advanceable within the elongate member. It should be noted that the strands may be individually enlarged to permit selective separation of the heart thereby lifting one side of the heart and rotating the heart to access the lateral surfaces and even the anterior surface of the heart. Furthermore, the strands 216 may be of different sizes as shown in FIG. 9A where the strands on the top of the device have a smaller expanded profile than the strands on the lower portion of the device.

In most variations, the stabilizing strands 216 designed to be atraumatic. For example, there may be a covering that prevents abrading or cutting of the anatomy that is separated by the strand 216. The space between the two sets of strands can be set based on the anatomic and/or procedure requirements.

Figure 9C:
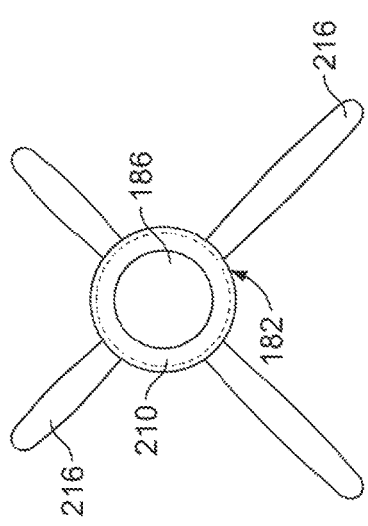
Figure 9D:
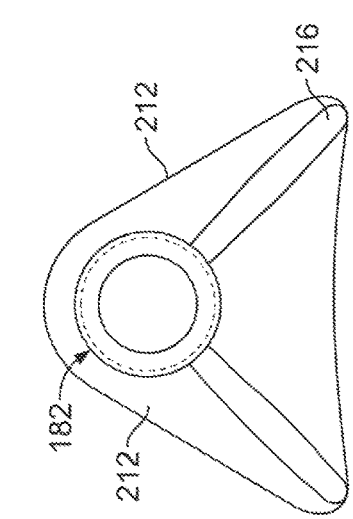

FIGS. 9C and 9D show another variation of an access device 182 comprising a balloon 212 surrounding two expandable strands 216. It should be noted that any number of expandable strands may be used. The balloon 212, in this configuration, is attached to the strands and defines a free balloon along the side opposite to the strands. As such, when the strands 216 expand they enlarge the balloon and contact the spine region to provide a stabilizing point. As the balloon inflates using inflation media delivered through the inflation lumen 214, the balloon also surrounds the organ being separated. This function provides an atraumatic surface while separating and stabilizing the organs. For example, as the balloon inflates to separate the heart from adjacent organs, inflation of the balloon forms an atraumatic surface to support the heart. It should be noted that this variation of the device 182 may also be used when rotated 180 degrees so the expandable strands support the heart and the free side of the balloon contacts the spine and esophagus. The balloon is attached to the guide tube distal and proximal to the strands to define a fluid impervious bond. It should be noted that the two strands may be individually actuated to permit selective separation of the heart thereby lifting one side of the heart and rotating the heart to access the lateral surfaces and even the anterior surface of the heart.

Figure 10C:
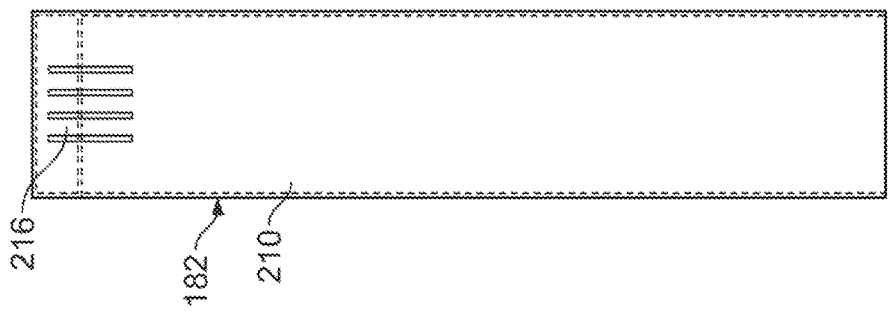
FIGS. 10A to 10C show a top view, a side view, and a bottom view of an access device having multiple stabilizer strands as expanding and stabilizing members.
Figure 10B:
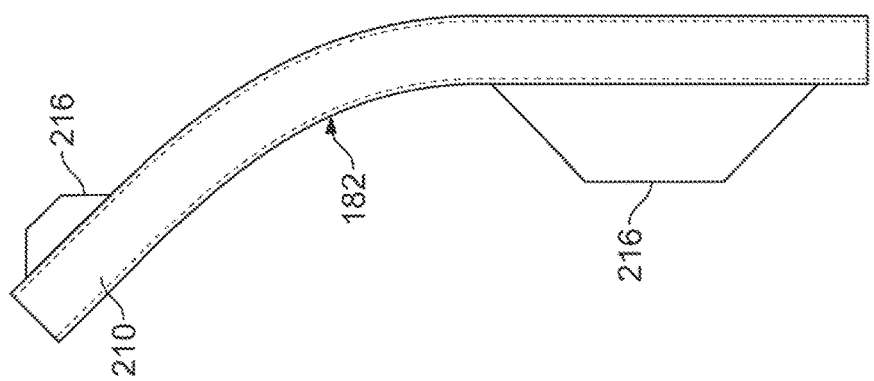
Figure 10A:
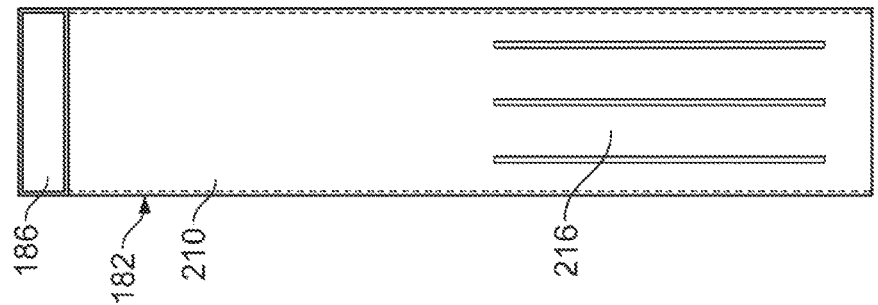

FIGS. 10A to 10C show an alternative variation of an access 182 where an expandable member comprises two sets of enlargeable strands 216, one set located towards a distal end of the device and a second set located proximally on the elongate member 210. The strands 216 may operate in any manner as described above. Variations of the device include sets of strands 216 that are offset either axially or radially from each other.

Figure 11B:
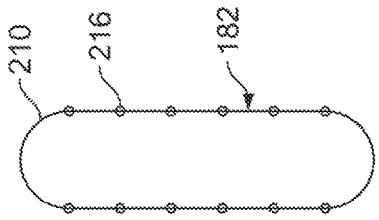
FIGS. 11A and 11B show a top view and a front view of an access device when the stabilizer members are in a compressed, low profile configuration.
Figure 11D:
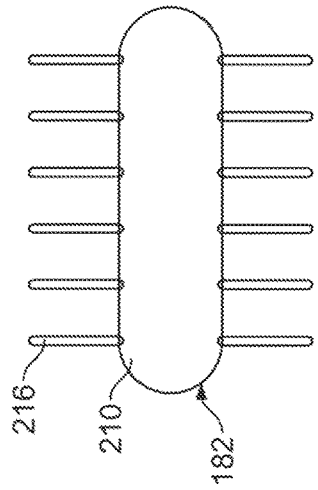
FIGS. 11C and 11D show a side view and a front view of the access device of FIGS. 11A and 11B in an expanded configuration.
Figure 11A:
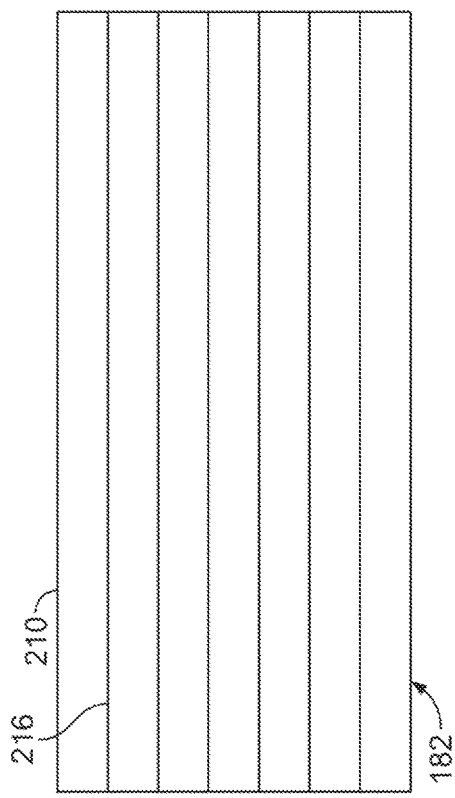
Figure 11C:
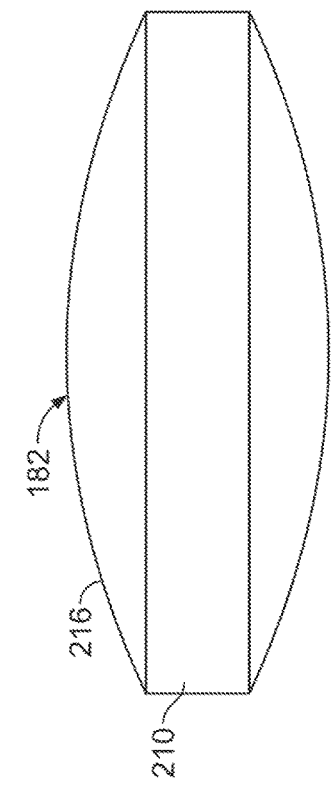

FIGS. 11A and 11B show an end portion of an access device 182 that comprises a series of enlargeable strands 216 along two sides of the elliptical elongate member 210. FIG. 11B shows the strands 216 in a compressed, low profile configuration. FIGS. 11C and 11D show a side and front view respectively of the access device 182 of FIGS. 11A and 11B. As shown, the strands are in an enlarged, expanded configuration. Again, the strands can be expanded as described above and define stabilizing surfaces to support the adjacent organs that are separated to produce the temporary cavity.

Figure 12A:
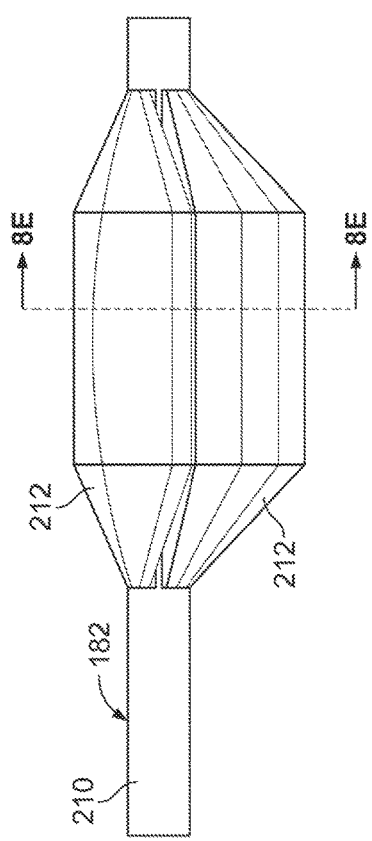
FIGS. 12A to 12C show a side view, an end view, and an isometric view of an access device having multiple balloons.
Figure 12C:
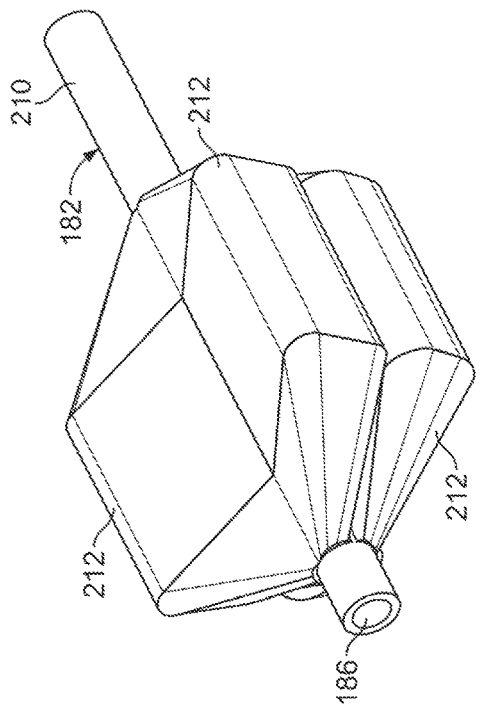
Figure 12B:
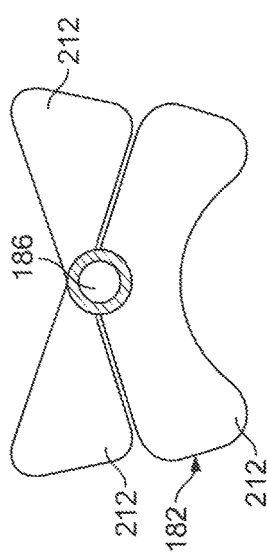

FIGS. 12A to 12C show another variation of an access device 182. In this variation, the device 182 incorporates three balloons 212 where two balloons 212 are oriented along the top of the elongate member 210 and a single balloon 212 is located at the bottom of the elongated 210. As shown, the balloons 212 may have pre-determined shapes that are useful when performing various procedures. For example, the bottom balloon 212 has a semi-circular groove on a surface that is opposite to the elongate member. This groove permits nesting of various organs (e.g., the spine or the esophagus) when creating the temporary cavity.

Figure 12D:
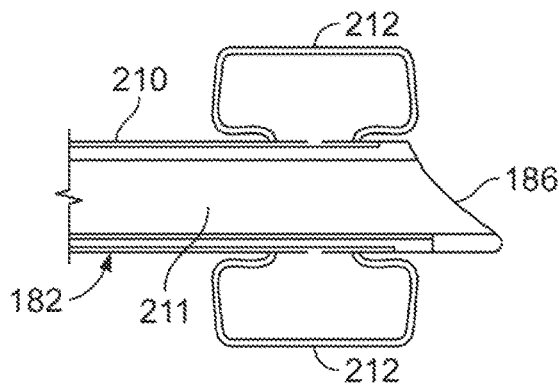
Figure 12E:
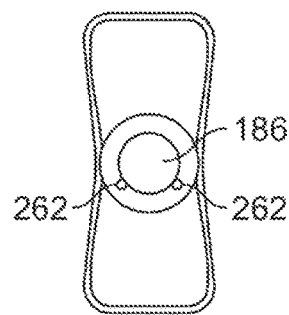
Figure 12F:
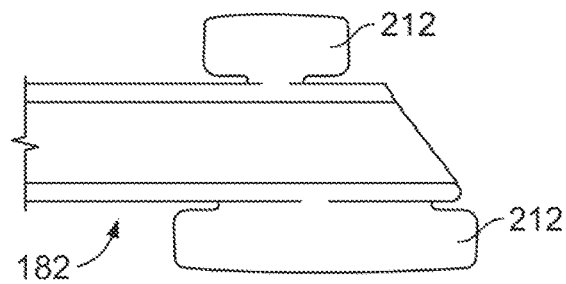

FIGS. 12D to 12F illustrate another variation of an access device 182. In this variation, the balloons 212 are selected to have a rectangular cross section when viewed co-axially along the elongate member 210 (as shown in FIG. 12D). Balloon 212 for use with the present device 182 may have any type of cross-section. As described below, the balloons may have varying shapes to accommodate certain organs or to create clearance at the opening 186 of the device 182. Such balloons may be pre-formed to a specific shape or cross-section. Furthermore, non-distensible balloons may also be employed with variations of the device.

FIG. 12D also shows the distal end of the elongate member 210 as being curved or angled to allow for a larger opening 186. Such a configuration permits greater access to the surface of the organ adjacent to the temporary cavity. As discussed above, the elongate member 210 may further include a plurality of aspiration/suction ports 262 located at an end of the device.

FIG. 12F illustrates yet another variation of an access device 182 where a length of one balloon member 212 is greater than the length of a second balloon member 212. Such a difference in length may be selected depending upon the desired procedure. In an alternate variation, a single balloon 212 may be employed where a portion of the balloon on one side of the elongate member 210 is shorter/longer than a portion of the same balloon on another side of the elongate member 210.

Figure 12G:
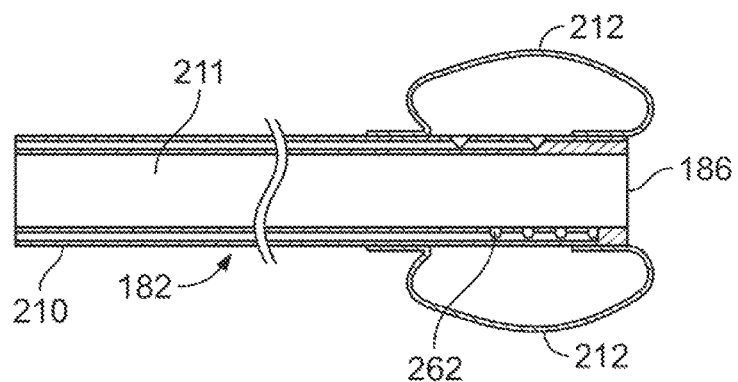
Figure 14E:
FIGS. 14E to 14G show side views of alternative dissecting jaw embodiments.
Figure 14F:
Figure 14G:
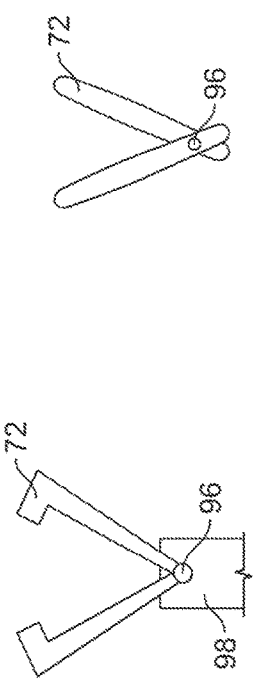
Figure 15A:
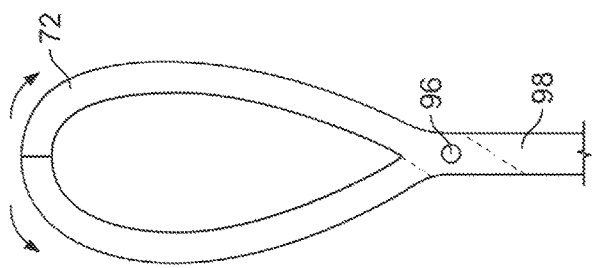
FIGS. 15A to 15D show side views of alternative dissecting jaw embodiments.
Figure 15B:
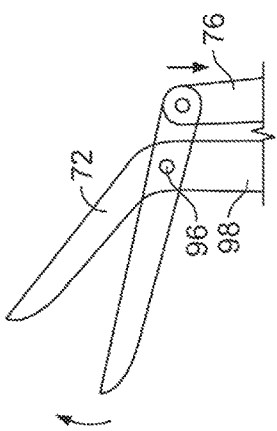
Figure 15C:
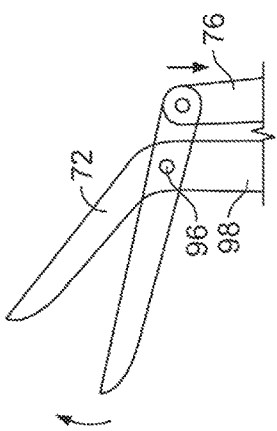
Figure 15D:
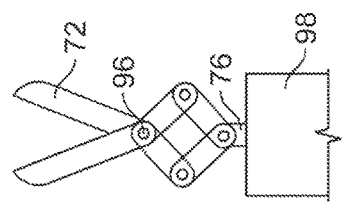
Figure 16A:
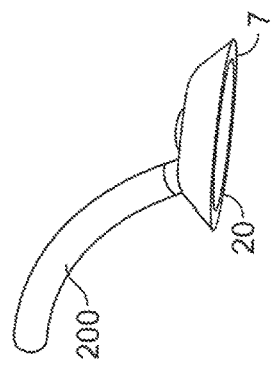
FIGS. 16A to 16D show a top view, a side view, a perspective view, and a bottom view of an appendage grasper embodiment.
Figure 16B:
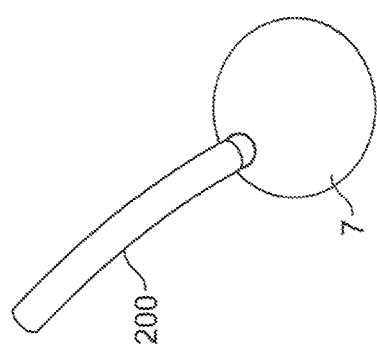
Figure 16C:
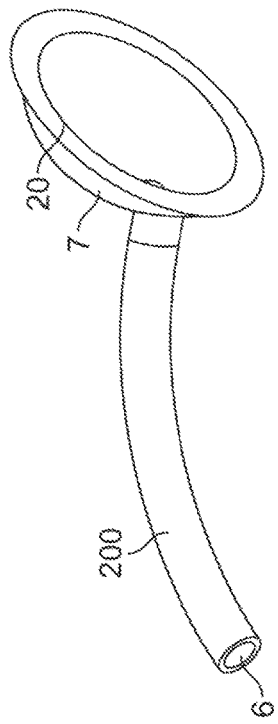
Figure 16D:
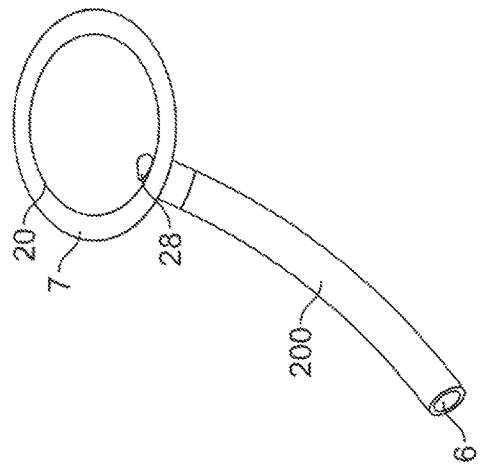

FIG. 12G shows a variation of an access device 182 where at least a portion of the balloon members 212 extend beyond the opening 186 of the elongate member 210. This configuration assists in spacing tissue from the opening 186 and reduces the probability that the tissue would otherwise obscure the visualization element (e.g., an endoscope) within the working channel 211 of the device 182. As shown, the device 182 may further include suction or aspiration ports 262 within the working channel 211 of the device and adjacent to the opening 186.

FIG. 12H illustrates a variation of an access device 182 in which the profile of the balloons 212 allows for clearance around the opening 186 of the working channel 211. Accordingly, a length of the balloon 212 adjacent to the elongate member 210 is less than a length of the balloon 212 at a surface away from the elongate member 212. FIG. 12H also shows a variation of the access device 182 as having locking members or balloons 264. The locking balloons 265 may be spaced from the distal end of the device 182 sufficiently so that upon inflation, they secure the device at the site by expanding within the body or outside of the body at the site of the incision. FIG. 12J shows a front view of the access device 182 of FIG. 12H. As shown, the end of the device 182 may include a suction/aspiration port 262 and a visualization/illumination element 246 that are spaced away from surrounding tissue due to the construction of the balloon 212.

FIG. 12J illustrates another variation of an access device 182 where the balloon members 212 are axially spaced along the elongate member 210.

Figure 18A:
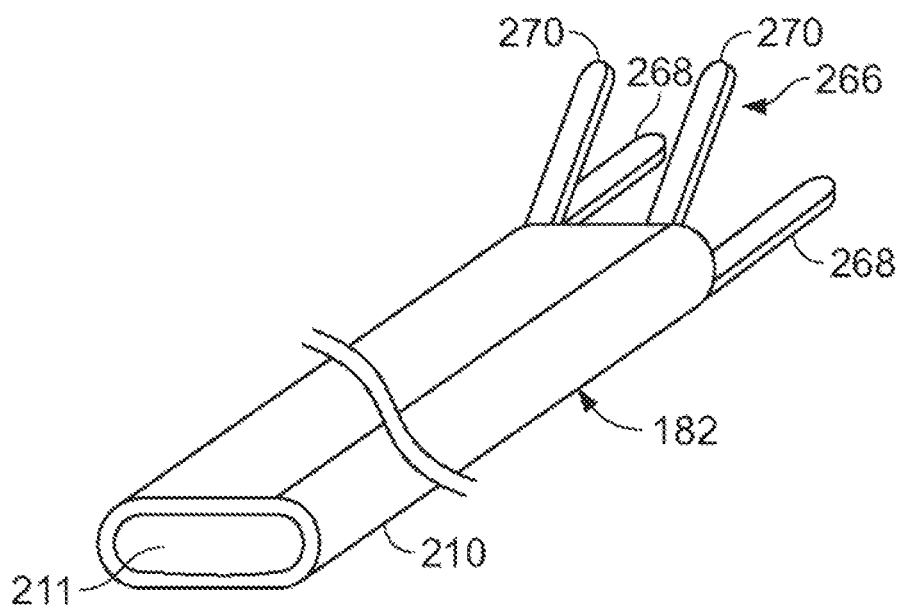
FIGS. 18A to 18C and 19A to 19B show additional variations of an access device where the expandable member is slidable out of the elongate member.
Figure 18B:
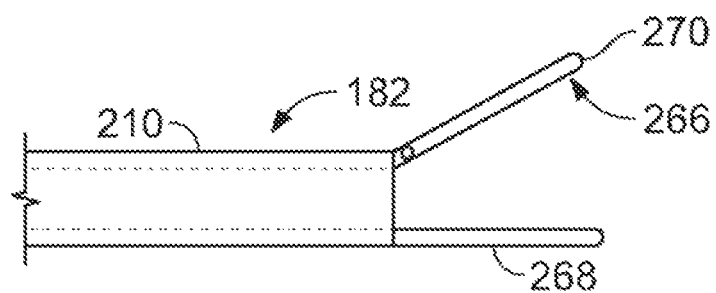
Figure 18C:
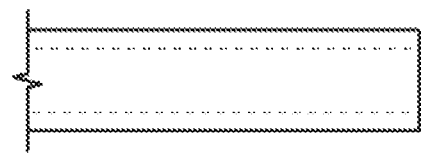

FIGS. 18A to 18C illustrates a variation of an access device 182 having an expandable member 266 that is slidable within the working channel 211 of the elongate member 210. As the expandable member 266 advances out of the elongate member 210, the expandable member expands in a manner that elevates and separates organs. As shown, the expandable member of FIG. 18A comprises a first and second set 268, 270 of arms. In this variation, the sets of arms 268, 270 expand in a non-uniform manner about the elongate 210 member. FIG. 18B shows a side view of the access device of FIG. 18A when the first and second set 268, 270 of the arms extends from the elongate member. FIG. 18C shows the first and second set 268, 270 of arms retracted within the elongate member 210.

Figure 19A:
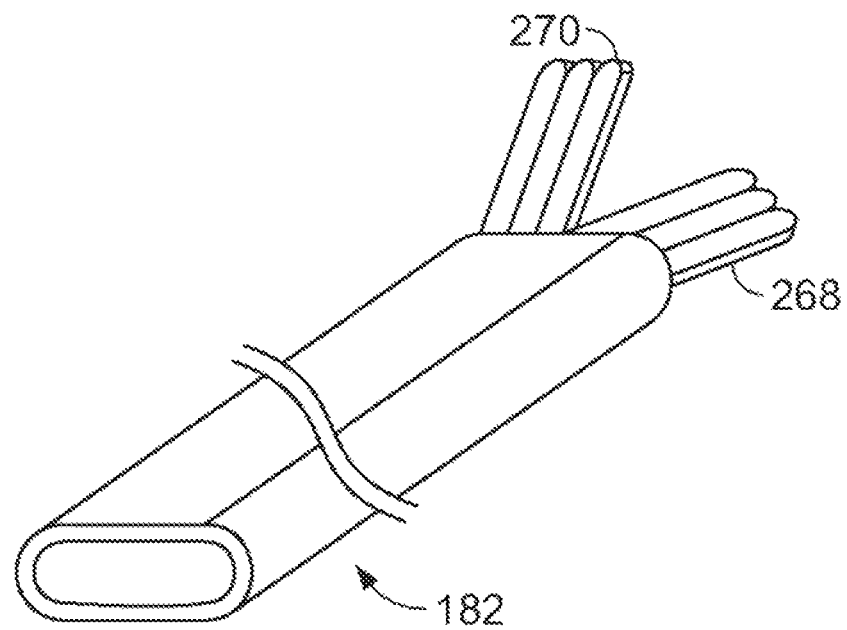
Figure 19B:
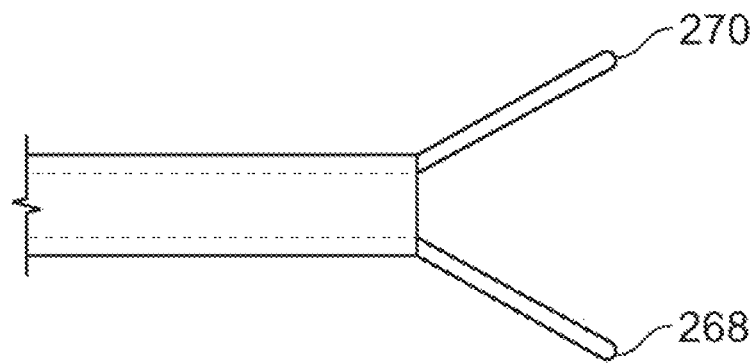

FIGS. 19A to 19B illustrate a variation of the access device 182 similar to the one shown in FIGS. 18A to 18C. However, in this variation, the access device 182 includes a first and second set 268, 270 of arms without spacing between the individual arms.

Figure 20A:
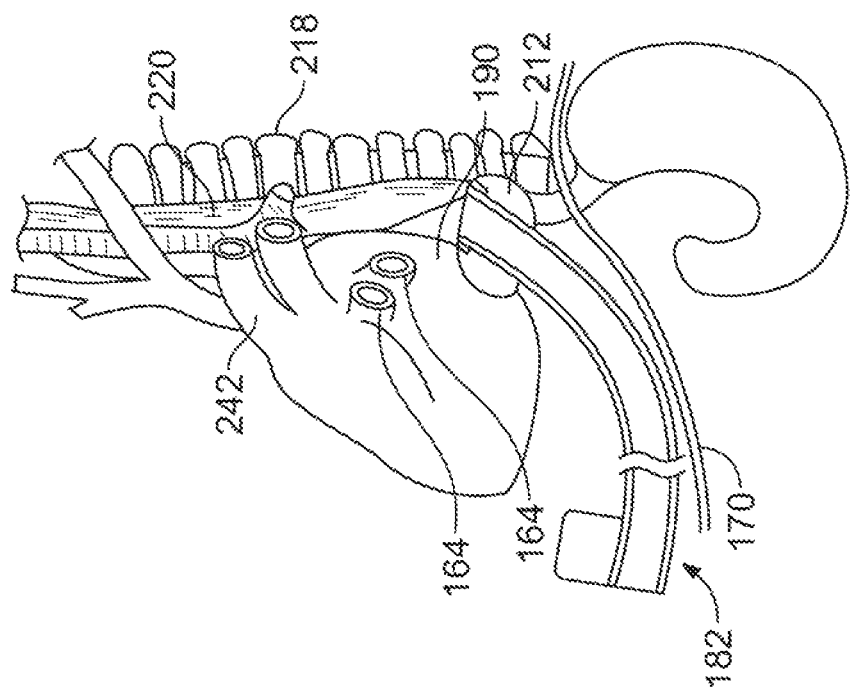
FIGS. 20A to 20B show an additional variation of an access device that is configured for use in a variety of traditional entry procedures.
Figure 20B:
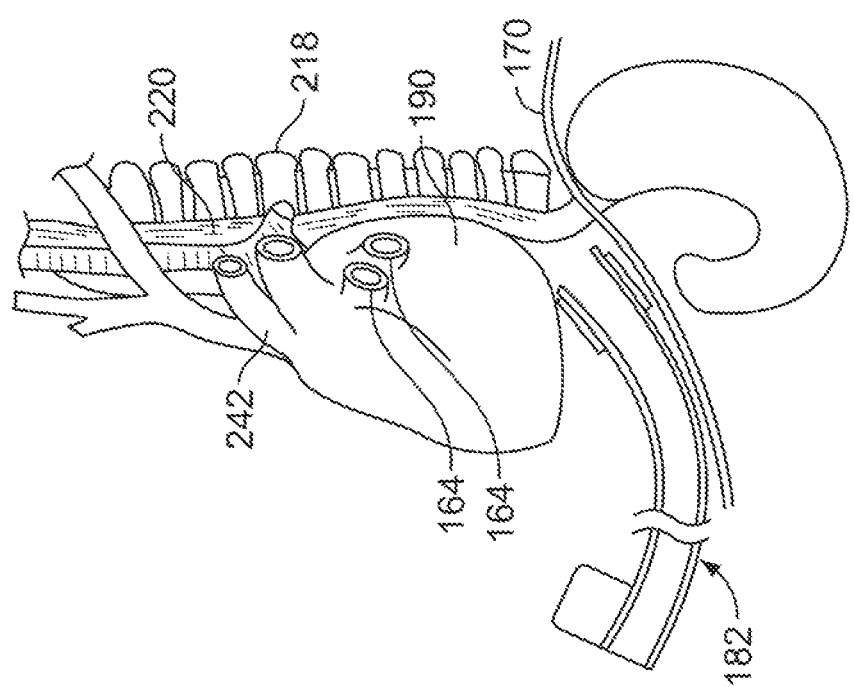

FIGS. 20A to 20B illustrate yet another variation of an access device 182. As shown in FIG. 20A, an access device 182 may also be used in parts of the body apart from the DEPA process. In this variation, the access device 182 has a curved shape to assist in positioning of the device 182 when advanced directly into the chest cavity during, for example, a sub-xyphoid approach as opposed to through the diaphragm 170. The shape of the access device 182 will vary depending on the procedure and intended entry procedure. As shown in FIG. 20B, once positioned, the expandable members 212 of the access device 182 may be inflated to elevate and separate organs to form a temporary cavity. Accordingly, variations of the present access devices 182 include elongate members that are curved, shapeable, or flexible to accommodate placement through the traditional entry techniques mentioned above.

Dissecting/Tunneling Embodiments

FIGS. 13A and 13B show the advantages of the DEPA process and associated dissecting/tunneling tool 124 device embodiments that provide direct visualization and exposure to the pericardial reflection in order that are designed to remove or separate adipose tissue (e.g. fat) and/or interconnective tissue from the heart to expose muscle layers and permit maneuvering the coagulation device or other instrumentation into engagement with heart tissue at any location, whether or not previously covered by fat or interconnective tissue.

FIGS. 14A to 14D show two side views and two cross-sectional views (at lines A-A and B-B respectively) of a dissecting/tunneling tool 124 embodiment capable of separating fat tissue. A shaft 98 supports two flexing segments 96, one at the proximal end adjacent to the handle 102 and the other at the distal end adjacent the dissecting legs 72. Four pull-wires 76 oriented at 90 degree intervals around a central axis are deflected by the handle and movement of the handle relative to the shaft at the proximal flex region 96 to cause the distal dissecting segment to correspondingly pivot at the distal flex region 96. As the shaft 98 is advanced the distal leg actuation 142 is advanced over the legs 72 to cause the legs to close and is retracted to urge the legs to open.

FIGS. 14E to 14G and 15A to 15D show alternative leg 72 and distal pivoting 96 configurations for various dissecting/tunneling instrument 124 embodiments.

Appendage Grasper/Positioner

FIGS. 16A to 16D show an appendage grasper 200 that stabilizes the atrial appendage and repositions the atrial appendage during the coagulation process and/or appendage isolation process. The appendage grasper 200 incorporates a vacuum lumen 6 that is coupled to a vacuum opening 28 in the covering 7 that defines an opening 20 that applies suction to the atrial appendage and pulls the atrial appendage into engagement with the grasper during manipulation of the atrial appendage.

Appendage Closure

FIGS. 17A to 17C show an appendage 250 that is closed with staples 194, snaps 196 or a clamp 198 during a DEPA process where diaphragm access to the posterior heart surface provides additional visualization of the left or right atrial appendage while closing the atrial appendage from the outside surface of the atrium. As described above, the separator/elevator may incorporate individually adjustable enlargement mechanisms (e.g. bladders or strands) to enable rotating the heart which provides additional access to the lateral surface of the heart. Augmenting this with thoracic access to the left atrial appendage enables grasping the appendage (e.g. with the grasper 200) and applying staples 194, snaps 196, a clamp 198, or other mechanism capable of closing the orifice of the atrial appendage and preventing blood inside the atrial appendage from communicating with (e.g. flowing into) the rest of the atrium.

Diaphragm Patch

A diaphragm patch measuring approximately 3 cm×3 cm may be used to close the diaphragm incision after the DEPA procedure has been completed and the incisions are to be closed. The patch may be fabricated from expanded PTFE, woven polyester, or other atraumatic polymer capable of being sewn or staples to the diaphragm such that when the entire circumference is sewn or staples, a fluid impervious surface is created along the DEPA incision through the diaphragm. The patch may also incorporate pledgeted outer surface to facilitate sewing and/or stapling and prevent bleeding during the patching step of the procedure.

Although the present inventions have been described in terms of the preferred embodiments above, numerous modifications and/or additions to the above-described preferred embodiments would be readily apparent to one skilled in the art. It is intended that the scope of the present inventions extend to all such modifications and/or additions and that the scope of the present inventions is limited solely by the claims of the invention.

Various kits can be sold that provide the practitioner with a complete system with which to perform a DEPA procedure. A separator/elevator, a coagulation device, an endoscope, a dissecting/tunneling instrument, trocars, a diaphragm patch, and staples to close the diaphragm opening may be incorporated into a kit used for atrial fibrillation or ventricular tachycardia treatment using a DEPA procedure.

What is claimed is:

1. A method of accessing posterior surfaces of a body organ in a in a thoracic cavity of a patient via a minimally invasive procedure, the method comprising:
    accessing a diaphragm through a first incision in an abdomen of the patient;
    creating an opening in the diaphragm;
    advancing an access device through the diaphragm into the thoracic cavity, such that the access device separates organs from the body organ within the thoracic cavity, where the access device comprises at least one working channel and an expandable member on an exterior of the access device; and
    actuating the expandable member to separate adjacent tissue structures to form a temporary cavity adjacent to the posterior surfaces of the body organ in the thoracic cavity.

2. The method of claim 1, where the access device is inserted into the body to the thoracic cavity in a generally straight profile.

3. The method of claim 1, further comprising coupling a visualization system to the working channel.

4. The method of claim 1, further comprising inserting a scope-type device into the working channel to provide visual access to the posterior surface of the body organ.

5. The method of claim 1, further comprising inserting at least one surgical instrument through the working channel into the temporary cavity.

6. The method of claim 1, where the expandable member comprises at least one balloon member.

7. The method of claim 1, further comprising performing a surgical procedure on or near the body organ.

8. The method of claim 7, further comprising creating at least a second incision in the patient to provide anterior visualization of the surgical procedure and where the access device provides posterior visualization of the surgical procedure.

9. The method of claim 1, where the expandable member on the access device conforms to the adjacent tissue structures while separating to stabilize the tissue structures.

10. The method of claim 1, where the access device further comprises an aspiration lumen.

11. The method of claim 1, where the body organ comprises the heart, and where the access device is placed in the thoracic cavity between the heart and spine.

12. The method of claim 11, where forming the temporary cavity comprises actuating the expandable member to separate the heart from an esophagus to expose a posterior surface of the heart.

13. The method of claim 12, where the access device provides direct visualization and access to the posterior surface of the heart.

14. The method of claim 12, further comprising creating a lesion on a side of a pulmonary vein without dissecting the pulmonary vein from a posterior surface of the heart.

15. The method of claim 1, further comprising creating a lesion on the posterior surface of the heart.

16. The method of claim 15, where creating the lesion on the posterior surface of the heart comprises creating the lesion between a superior vena cava and a pulmonary vein.

17. The method of claim 1, further comprising creating a lesion on the posterior surface of the heart adjacent to a pulmonary vein without dissecting the pulmonary vein from cardiac tissue.

18. The method of claim 1, where the body organ comprises the esophagus, and where the access device is placed behind the esophagus.

19. The method of claim 18, where forming a temporary cavity comprises actuating the expandable member to separate the esophagus from esophageal vessels.

20. The method of claim 1, where the expandable member expands in a non-uniform radial direction from the elongate member to create the temporary cavity.

* * * * *